US008272872B2

(12) United States Patent
Utter et al.

(10) Patent No.: US 8,272,872 B2
(45) Date of Patent: *Sep. 25, 2012

(54) SYSTEM AND METHOD FOR CALCULATING OPTIMAL PERFORMANCE AND WEIGHT CLASSIFICATION

(75) Inventors: Alan Utter, Boone, NC (US); David Nieman, Boone, NC (US); Mark Brittingham, Califon, NJ (US)

(73) Assignee: National Wrestling Coaches Association, Manheim, PA (US)

( * ) Notice: Subject to any disclaimer, the term of this patent is extended or adjusted under 35 U.S.C. 154(b) by 1064 days.

This patent is subject to a terminal disclaimer.

(21) Appl. No.: 11/861,069

(22) Filed: Sep. 25, 2007

(65) Prior Publication Data

US 2008/0140713 A1 Jun. 12, 2008

Related U.S. Application Data

(63) Continuation-in-part of application No. 10/446,086, filed on May 28, 2003, now abandoned, which is a continuation-in-part of application No. 10/355,195, filed on Jan. 31, 2003, now Pat. No. 7,247,023.

(60) Provisional application No. 60/391,587, filed on Jun. 27, 2002, provisional application No. 60/826,865, filed on Sep. 25, 2006, provisional application No. 60/864,609, filed on Nov. 7, 2006.

(51) Int. Cl.
*G09B 19/00* (2006.01)
(52) U.S. Cl. ........ 434/127; 434/236; 434/365; 600/300; 128/921
(58) Field of Classification Search .................. 434/127, 434/238
See application file for complete search history.

(56) References Cited

U.S. PATENT DOCUMENTS

| | | | | |
|---|---|---|---|---|
| 895,128 | A * | 8/1908 | Trant | 273/243 |
| 4,273,337 | A * | 6/1981 | Carrera et al. | 273/243 |
| 5,010,580 | A * | 4/1991 | Vincent et al. | 382/163 |
| 5,062,645 | A * | 11/1991 | Goodman et al. | 273/249 |
| 5,244,391 | A * | 9/1993 | Bryant | 434/129 |
| 5,412,560 | A * | 5/1995 | Dennison | 600/300 |
| 5,435,315 | A * | 7/1995 | McPhee et al. | 600/483 |
| 5,454,721 | A * | 10/1995 | Kuch | 454/127 |
| 5,704,611 | A * | 1/1998 | Pierce | 273/243 |
| 5,796,640 | A * | 8/1998 | Sugarman et al. | 708/132 |
| 5,839,901 | A * | 11/1998 | Karkanen | 434/127 |
| 6,233,539 | B1 * | 5/2001 | Brown | 703/11 |
| 6,279,908 | B1 * | 8/2001 | Hunsberger | 273/249 |
| 6,553,386 | B1 * | 4/2003 | Alabaster | 1/1 |

(Continued)

OTHER PUBLICATIONS

2001 NCAA Wrestling Rules and Interpretation. National Collegiate Athletic Association.*

(Continued)

*Primary Examiner* — Robert J Utama
(74) *Attorney, Agent, or Firm* — Baker Donelson Bearman Caldwell and Berkowitz, PC

(57) ABSTRACT

A website providing a weight, activity and nutritional program over a network. The website allows users to input an assessment of a subject, which can be used to generate a condition overview and a weight plan for the subject. The weight plan can include minimum weights for the subject, each of the minimum weights being associated with a time. The website can also be used to generate a nutrition plan based on the subject data entered, and to enter and monitor activity data.

19 Claims, 27 Drawing Sheets

U.S. PATENT DOCUMENTS

| | | | | |
|---|---|---|---|---|
| 6,585,516 | B1* | 7/2003 | Alabaster | 434/127 |
| 6,669,196 | B1* | 12/2003 | Washko | 273/243 |
| 6,872,077 | B2* | 3/2005 | Yeager | 434/127 |
| 7,778,845 | B2* | 8/2010 | Brown | 705/2 |
| 2002/0193702 | A1* | 12/2002 | Yamazaki et al. | 600/547 |
| 2003/0167020 | A1* | 9/2003 | Kawanishi et al. | 600/547 |
| 2003/0229275 | A1* | 12/2003 | Koyama et al. | 600/300 |
| 2004/0054111 | A1* | 3/2004 | Kalantar et al. | 526/347 |
| 2004/0077955 | A1* | 4/2004 | Kawanishi et al. | 600/483 |

OTHER PUBLICATIONS

Lukasi et al. Assessment of Fat-free mass using bioelectrical impedance measurements of the human body. The American Journal of Clinical Nutrition, Apr. 1985, p. 810-817.*

Elis Et al. Monitoring Childhood Obesity: Assessment of the Weight/Height Index. American Journal of Epidemiology. Feb. 18, 1999.*

* cited by examiner

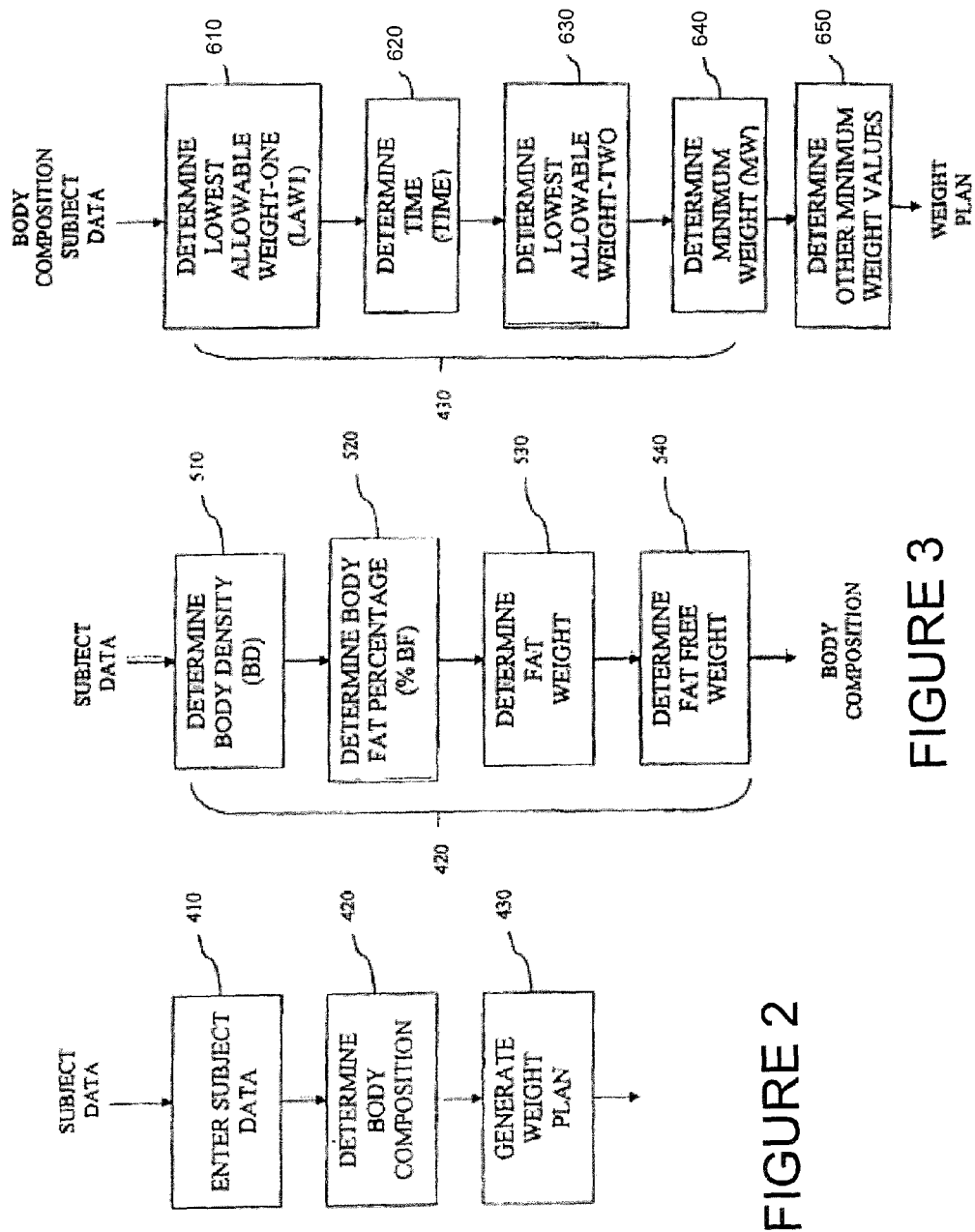

Weight Assessment 2006-07 Student Weight Assessment

PLEASE USE YOUR TAB BUTTON TO MOVE FROM FIELD TO FIELD IN COMPLETING THE ASSESSMENT FORM

Name of Student (first, last) Nico    Angelo
School Name: OREGON PE TEST, OR
Gender: Male    Grade: 10

CALCULATION OF ASSESSMENT

Date Of Assessment    9/24/2006

Age 15

| Measurement | Value | Rank (Percent) |
|---|---|---|
| Weight (lbs.) | 140 | 62 |
| Height | 5 (feet) 4.00 (inches) | 51 |
| BMI | 24.0307 | 63 |
| Waist Circumference (inches) | 32 | 64 |
| Triceps (T) | 19 | 56 |
| Subscapular (S) | 19 | 78 |
| Weight and Body Composition Ranking | | 64.7 |
| Classification | | normal |

*STEP 2: Target Weight (TW) = tbd*

[Print & Save]  [Save]  [Main Menu]  [Re-Calculate]

Export Usernames/Passwords to Excel | Export Students on File to Excel

NWCA Optimal Performance Calculator
Students On File Report
Date: 9/25/2006

Students Currently on File For: OREGON PE TEST

| Wrestler Name | School Grade | Alpha Date | Alpha Weight | Letter Weight | New Assessment | Previous Assessment | Assessment Report Summary | Wt. Loss Plan | View Activities | Login ID | Password |
|---|---|---|---|---|---|---|---|---|---|---|---|
| Angelo, Nico | 12 | 9/24/2006 | 140 | 140 | Select | Select | Select | Select | Select | 61501-11 | oNA4165 |
| Angelo, Nico | 12 | 9/23/2006 | 145 | 145 | Select | Select | Select | Select | Select | 61501-11 | oNA4165 |
| H, J | 5 | | | | Select | Select | Select | Select | Select | 61501-10 | hJH3044 |
| Hork, James | 4 | | | | Select | Select | Select | Select | Select | 61501-18 | kJH9622 |
| Jenkins, ABC | 5 | 7/6/2006 | 125 | 0 | Select | Select | Select | Select | Select | 61501-03 | sAJ1115 |
| Jenkins, ABC123 | 9 | 7/25/2006 | 123 | 125 | Select | Select | Select | Select | Select | 61501-02 | sAJ3053 |
| Jenkins, ABC123 | 9 | 8/2/2006 | 125 | 125 | Select | Select | Select | Select | Select | 61501-02 | sAJ3053 |
| Jenkins, ABC123 | 9 | 7/8/2006 | 125 | 0 | Select | Select | Select | Select | Select | 61501-02 | sAJ3053 |
| Jenkins, ABC123 | 9 | 9/1/2006 | 220 | 212 | Select | Select | Select | Select | Select | 61501-02 | sAJ3053 |
| Jenkins, XYZ | 8 | | | | Select | Select | Select | Select | Select | 61501-01 | sAJ4099 |
| Marco, Vincenzo | 11 | | | | Select | Select | Select | Select | Select | 61501-13 | oVM3677 |
| Monday, Test | 12 | 9/25/2006 | 150 | 150 | Select | Select | Select | Select | Select | 61501-16 | yTM7192 |
| Moyer, Michael | 11 | 9/25/2006 | 150 | 150 | Select | Select | Select | Select | Select | 61501-15 | mMM0247 |
| Moyer, Mike | 8 | 9/29/2006 | 110 | 110 | Select | Select | Select | Select | Select | 61501-08 | rMM8247 |
| smith, joe | 8 | 8/11/2006 | 120 | 120 | Select | Select | Select | Select | Select | 61501-05 | hs5989 |
| Testz, Monday | 12 | 9/25/2006 | 300 | 300 | Select | Select | Select | Select | Select | 61501-17 | 2MT3315 |
| Tocci, Pat | 10 | 9/14/2006 | 150 | 150 | Select | Select | Select | Select | Select | 61501-07 | PT4561 |
| Tocci, Pat | 10 | 10/7/2006 | 143 | 139 | Select | Select | Select | Select | Select | 61501-04 | PT6293 |
| Tocci, Pat | 10 | 12/7/2006 | 141 | 141 | Select | Select | Select | Select | Select | 61501-04 | PT6293 |
| Tocci, Pat | 10 | 8/9/2006 | 145 | 141 | Select | Select | Select | Select | Select | 61501-04 | PT6293 |
| Utter, Alan | 6 | 8/15/2006 | 160 | 156 | Select | Select | Select | Select | Select | 61501-06 | tAU0010 |
| Vincenzo, Marco | 11 | 9/24/2006 | 145 | 145 | Select | Select | Select | Select | Select | 61501-12 | oMV4441 |
| Woo, Angelo | 12 | 9/24/2006 | 170 | 170 | Select | Select | Select | Select | Select | 61501-14 | oAV2477 |

Return to Main

FIGURE 7

| | WEIGHT (lbs) | 155 | <- ENTER WEIGHT | | | |
|---|---|---|---|---|---|---|
| | TIME (min) | 80 | <- ENTER ACTIVITY DURATION | | | |
| act_id | mets | cals_kg | ??? | gen_cat | act_cat | act_describ |
| 1 | 8.5 | 0.14875 | 629 | 1 | BICYCLING | BICYCLING, BMX OR MOUNTAIN |
| 2 | 4 | 0.07 | 296 | 1 | BICYCLING | BICYCLING, < 10 MPH, LEISURE, TO WORK OR FOR PLEASURE |
| 3 | 8 | 0.14 | 592 | 1 | BICYCLING | BICYCLING, GENERAL |
| 4 | 6 | 0.105 | 444 | 1 | BICYCLING | BICYCLING, 10-11.9 MPH, LEISURE, SLOW, LIGHT EFFORT |
| 5 | 8 | 0.14 | 592 | 1 | BICYCLING | BICYCLING, 12-13.9 MPH, LEISURE, MODERATE EFFORT |
| 6 | 10 | 0.175 | 740 | 1 | BICYCLING | BICYCLING, 14-15.9 MPH, RACING OR LEISURE, FAST, VIGOROUS EFFORT |
| 7 | 12 | 0.21 | 888 | 1 | BICYCLING | BICYCLING, 16-19 MPH, RACING/ NOT DRAFTING OR > 19 MPH DRAFTING, VERY FAST, RACING GENERAL |
| 8 | 16 | 0.28 | 1184 | 1 | BICYCLING | BICYCLING, >20 MPH, RACING, NOT DRAFTING |
| 10 | 7 | 0.1225 | 518 | 1 | BICYCLING - STATIONARY | BICYCLING, STATIONARY, GENERAL |
| 11 | 3 | 0.0525 | 222 | 1 | BICYCLING - STATIONARY | BICYCLING, STATIONARY, 50 WATTS, VERY LIGHT EFFORT |
| 12 | 5.5 | 0.09625 | 407 | 1 | BICYCLING - STATIONARY | BICYCLING, STATIONARY, 100 WATTS, LIGHT EFFORT |
| 13 | 7 | 0.1225 | 518 | 1 | BICYCLING - STATIONARY | BICYCLING, STATIONARY, 150 WATTS, MODERATE EFFORT |
| 14 | 10.5 | 0.18375 | 777 | 1 | BICYCLING - STATIONARY | BICYCLING, STATIONARY, 200 WATTS, VIGOROUS EFFORT |
| 15 | 12.5 | 0.21875 | 925 | 1 | BICYCLING - STATIONARY | BICYCLING, STATIONARY, 250 WATTS, VERY VIGOROUS EFFORT |
| 16 | 8 | 0.14 | 592 | 4 | STRENGTH TRAINING | CALISTHENICS (E.G. PUSHUPS, SITUPS, PULLUPS, JUMPING JACKS), HEAVY, VIGOROUS EFFORT |
| 17 | 3.5 | 0.06125 | 259 | 4 | STRENGTH TRAINING | CALISTHENICS, HOME EXERCISE, LIGHT OR MODERATE EFFORT, GENERAL (EXAMPLE: BACK EXERCISES) |
| 18 | 8 | 0.14 | 592 | 1 | MISC. AEROBIC | CIRCUIT TRAINING, INCLUDING SOME AEROBIC MOVEMENT WITH MINIMAL REST, GENERAL |
| 19 | 6 | 0.105 | 444 | 4 | STRENGTH TRAINING | WEIGHT LIFTING (FREE WEIGHT, NAUTILUS OR UNIVERSAL-TYPE), POWER LIFTING OR BODY BUILDING, VIGOROUS EFFORT |
| 20 | 5.5 | 0.09625 | 407 | 4 | STRENGTH TRAINING | HEALTH CLUB EXERCISE, GENERAL |
| 21 | 9 | 0.1575 | 666 | 1 | STEPPER | STAIR-TREADMILL ERGOMETER, GENERAL |
| 22 | 7 | 0.1225 | 518 | 1 | ROWING - STATIONARY | ROWING, STATIONARY ERGOMETER, GENERAL |
| 23 | 3.5 | 0.06125 | 259 | 1 | ROWING - STATIONARY | ROWING - STATIONARY, 50 WATTS, LIGHT EFFORT |
| 24 | 7 | 0.1225 | 518 | 1 | ROWING - STATIONARY | ROWING, STATIONARY, 100 WATTS, MODERATE EFFORT |
| 25 | 8.5 | 0.14875 | 629 | 1 | ROWING - STATIONARY | ROWING, STATIONARY, 150 WATTS, VIGOROUS EFFORT |
| 26 | 12 | 0.21 | 888 | 1 | ROWING - STATIONARY | ROWING, STATIONARY, 200 WATTS, VERY VIGOROUS EFFORT |
| 27 | 7 | 0.1225 | 518 | 1 | MISC. AEROBIC | SKI MACHINE, GENERAL |
| 28 | 2.5 | 0.04375 | 185 | 5 | STRETCHING | STRETCHING, HATHA YOGA |
| 30 | 2.5 | 0.04375 | 185 | 5 | STRETCHING | MILD STRETCHING |
| 31 | 6 | 0.105 | 444 | 1 | MISC. AEROBIC | TEACHING AEROBIC EXERCISE CLASS |
| 32 | 4 | 0.07 | 296 | 1 | GROUP EXERCISE | WATER AEROBICS, WATER CALISTHENICS |
| 33 | 3 | 0.0525 | 222 | 4 | STRENGTH TRAINING | WEIGHT LIFTING (FREE, NAUTILUS OR UNIVERSAL-TYPE), LIGHT OR MODERATE EFFORT, LIGHT WORKOUT, GENERAL |

FIG. 8A  TO FIG. 8B

FROM FIG. 8A

| # | | | | Category | Activity |
|---|---|---|---|---|---|
| 34 | 1 | 0.0175 | 74 | GENERAL ACTIVITY | WHIRLPOOL, SITTING |
| 35 | 5 | 0.084 | 355 | DANCING | BALLET, OR MODERN, TWIST, JAZZ, TAP, JITTERBUG |
| 36 | 6 | 0.11375 | 481 | GROUP EXERCISE | AEROBICS, GENERAL |
| 37 | 8 | 0.14675 | 629 | GROUP EXERCISE | AEROBICS, STEP WITH 6 - 8 INCH STEP |
| 38 | 10 | 0.175 | 740 | GROUP EXERCISE | AEROBICS, STEP WITH 10 - 12 INCH STEP |
| 39 | 5 | 0.0875 | 370 | GROUP EXERCISE | AEROBICS, LOW IMPACT |
| 40 | 7 | 0.1225 | 618 | GROUP EXERCISE | AEROBICS, HIGH IMPACT |
| 41 | 4 | 0.07875 | 333 | DANCING | GENERAL, GREEK, MIDDLE EASTERN, HULA, FLAMENCO, BELLY, AND SWING DANCING |
| 42 | 8 | 0.09825 | 407 | DANCING | BALLROOM, DANCING FAST |
| 43 | 4 | 0.07875 | 333 | DANCING | BALLROOM, FAST (DISCO, FOLK, SQUARE), LINE DANCING, IRISH STEP DANCING, POLKA, CONTRA, COUNTRY |
| 44 | 3 | 0.0525 | 222 | DANCING | BALLROOM, SLOW (E.G. WALTZ, FOXTROT, SLOW DANCING), SAMBA, TANGO, 19TH C, MAMBO, CHACHA |
| 45 | 6 | 0.09925 | 407 | DANCING | ANISHINSABE JINGLE DANCING OR OTHER TRADITIONAL AMERICAN INDIAN DANCING |
| 46 | 3 | 0.0525 | 222 | FISHING | FISHING, GENERAL |
| 47 | 4 | 0.07 | 296 | FISHING | DIGGING WORMS, WITH SHOVEL |
| 48 | 4 | 0.07 | 296 | FISHING | FISHING FROM RIVER BANK AND WALKING |
| 49 | 2 | 0.04375 | 185 | FISHING | FISHING FROM BOAT, SITTING |
| 50 | 4 | 0.06125 | 259 | FISHING | FISHING FROM RIVER BANK, STANDING |
| 51 | 6 | 0.105 | 444 | FISHING | FISHING IN STREAM, IN WADERS |
| 52 | 2 | 0.035 | 148 | FISHING | FISHING, ICE, SITTING |
| 53 | 2 | 0.04375 | 185 | HUNTING | HUNTING, BOW AND ARROW OR CROSSBOW |
| 54 | 6 | 0.105 | 444 | HUNTING | HUNTING, DEER, ELK, LARGE GAME |
| 55 | 2 | 0.04375 | 185 | HUNTING | HUNTING, DUCK, WADING |
| 56 | 5 | 0.0875 | 370 | HUNTING | HUNTING, GENERAL |
| 57 | 6 | 0.105 | 444 | HUNTING | HUNTING, PHEASANTS OR GROUSE |
| 58 | 5 | 0.0875 | 370 | HUNTING | HUNTING, RABBIT, SQUIRREL, PRAIRIE CHICK, RACCOON, SMALL GAME |
| 59 | 2 | 0.04375 | 185 | HUNTING | PISTOL SHOOTING OR TRAP SHOOTING, STANDING |
| 60 | 3 | 0.05775 | 244 | HOME ACTIVITIES | CARPET SWEEPING, SWEEPING FLOORS |
| 61 | 3 | 0.0525 | 222 | HOME ACTIVITIES | CLEANING, HEAVY OR MAJOR (E.G. WASH CAR, WASH WINDOWS, CLEAN GARAGE), VIGOROUS EFFORT |
| 62 | 4 | 0.06125 | 259 | HOME ACTIVITIES | MOPPING |
| 63 | 2 | 0.04375 | 185 | HOME ACTIVITIES | MULTIPLE HOUSEHOLD TASKS ALL AT ONCE, LIGHT EFFORT |
| 64 | 4 | 0.06125 | 259 | HOME ACTIVITIES | MULTIPLE HOUSEHOLD TASKS ALL AT ONCE, MODERATE EFFORT |

FIG. 8B   TO FIG. 8C

FROM FIG. 8B

| # | | | | Category | Description |
|---|---|---|---|---|---|
| 65 | 4 | 0.07 | 296 | 3 | HOME ACTIVITIES | MULTIPLE HOUSEHOLD TASKS ALL AT ONCE, VIGOROUS EFFORT |
| 66 | 3 | 0.0525 | 222 | 3 | HOME ACTIVITIES | CLEANING, HOUSE OR CABIN, GENERAL |
| 67 | 2 | 0.04375 | 185 | 7 | HOME ACTIVITIES | CLEANING, LIGHT (DUSTING, STRAIGHTENING UP, CHANGING LINEN, CARRYING OUT TRASH) |
| 68 | 2 | 0.04025 | 170 | 7 | HOME ACTIVITIES | WASH DISHES - STANDING OR IN GENERAL (NOT BROKEN INTO STAND/WALK COMPONENTS) |
| 69 | 2 | 0.04375 | 185 | 3 | HOME ACTIVITIES | WASH DISHES - CLEARING DISHES FROM TABLE - WALKING |
| 70 | 4 | 0.06125 | 259 | 3 | HOME ACTIVITIES | VACUUMING |
| 71 | 6 | 0.105 | 444 | 7 | HOME ACTIVITIES | BUTCHERING ANIMALS |
| 72 | 2 | 0.035 | 148 | 3 | HOME ACTIVITIES | COOKING OR FOOD PREPARATION - STANDING OR SITTING OR IN GENERAL (NOT BROKEN INTO STAND/WALK COMPONENTS), MANUAL APPLIANCES |
| 73 | 2 | 0.04375 | 185 | 7 | HOME ACTIVITIES | SERVING FOOD, SETTING TABLE - IMPLIED WALKING OR STANDING |
| 74 | 2 | 0.04375 | 185 | 7 | HOME ACTIVITIES | COOKING OR FOOD PREPARATION - WALKING |
| 75 | 2 | 0.04375 | 185 | 7 | HOME ACTIVITIES | FEEDING ANIMALS |
| 76 | 2 | 0.04375 | 185 | 7 | HOME ACTIVITIES | PUTTING AWAY GROCERIES (E.G. CARRYING GROCERIES, SHOPPING WITHOUT A GROCERY CART), CARRYING PACKAGES |
| 77 | 8 | 0.13125 | 555 | 3 | HOME ACTIVITIES | CARRYING GROCERIES UPSTAIRS |
| 78 | 3 | 0.0525 | 222 | 3 | HOME ACTIVITIES | COOKING INDIAN BREAD ON AN OUTSIDE STOVE |
| 79 | 2 | 0.04025 | 170 | 7 | HOME ACTIVITIES | FOOD SHOPPING WITH OR WITHOUT A GROCERY CART, STANDING OR WALKING |
| 80 | 2 | 0.04025 | 170 | 7 | HOME ACTIVITIES | NON-FOOD SHOPPING, STANDING OR WALKING |
| 81 | 2 | 0.04025 | 170 | 7 | HOME ACTIVITIES | WALKING - SHOPPING (NON-GROCERY SHOPPING) |
| 82 | 2 | 0.04025 | 170 | 7 | HOME ACTIVITIES | IRONING |
| 83 | 2 | 0.02625 | 111 | 7 | HOME ACTIVITIES | SITTING - KNITTING, SEWING, LT. WRAPPING (PRESENTS) |
| 84 | 2 | 0.035 | 148 | 7 | HOME ACTIVITIES | IMPLIED STANDING - LAUNDRY, FOLD OR HANG CLOTHES, PUT CLOTHES IN WASHER OR DRYER, PACKING SUITCASE |
| 85 | 2 | 0.04025 | 170 | 7 | HOME ACTIVITIES | IMPLIED WALKING - PUTTING AWAY CLOTHES, GATHERING CLOTHES TO PACK, PUTTING AWAY LAUNDRY |
| 86 | 2 | 0.035 | 148 | 7 | HOME ACTIVITIES | MAKING BED |
| 87 | 5 | 0.0875 | 370 | 7 | HOME ACTIVITIES | MAPLE SYRUPING/SUGAR BUSHING (INCLUDING CARRYING BUCKETS, CARRYING WOOD) |
| 88 | 6 | 0.105 | 444 | 3 | HOME ACTIVITIES | MOVING FURNITURE, HOUSEHOLD ITEMS, CARRYING BOXES |
| 89 | 4 | 0.0565 | 281 | 3 | HOME ACTIVITIES | SCRUBBING FLOORS, ON HANDS AND KNEES, SCRUBBING BATHROOM, BATHTUB |
| 90 | 4 | 0.07 | 296 | 3 | HOME ACTIVITIES | SWEEPING GARAGE, SIDEWALK OR OUTSIDE OF HOUSE |
| 91 | 7 | 0.1225 | 518 | 3 | HOME ACTIVITIES | MOVING HOUSEHOLD ITEMS, CARRYING BOXES |
| 92 | 4 | 0.06125 | 259 | 3 | HOME ACTIVITIES | STANDING - PACKING/UNPACKING BOXES, OCCASIONAL LIFTING OF HOUSEHOLD ITEMS LIGHT - MODERATE EFFORT |
| 93 | 3 | 0.0525 | 222 | 3 | HOME ACTIVITIES | IMPLIED WALKING - PUTTING AWAY HOUSEHOLD ITEMS - MODERATE EFFORT |
| 94 | 2 | 0.04375 | 185 | 7 | HOME ACTIVITIES | WATERING PLANTS |
| 95 | 2 | 0.04375 | 185 | 7 | HOME ACTIVITIES | BUILDING A FIRE INSIDE |

FIG. 8C    TO FIG. 8D

FROM FIG. 8C

| | | | | | |
|---|---|---|---|---|---|
| 96 | 9 | 0.1575 | 666 | 3 | HOME ACTIVITIES | MOVING HOUSEHOLD ITEMS UPSTAIRS, CARRYING BOXES OR FURNITURE |
| 97 | 2 | 0.035 | 148 | 7 | HOME ACTIVITIES | STANDING - LIGHT (PUMP GAS, CHANGE LIGHTBULB, ETC.) |
| 98 | 3 | 0.0525 | 222 | 3 | HOME ACTIVITIES | WALKING - LIGHT NONCLEANING (READYING TO LEAVE, SHUT/LOCK DOORS, CLOSE WINDOWS, ETC.) |
| 99 | 2 | 0.04375 | 185 | 7 | HOME ACTIVITIES | SITTING - PLAYING WITH CHILD(REN) - LIGHT, ONLY ACTIVE PERIODS |
| 100 | 3 | 0.049 | 207 | 3 | HOME ACTIVITIES | STANDING - PLAYING WITH CHILDREN - LIGHT, ONLY ACTIVE PERIODS |
| 101 | 4 | 0.07 | 296 | 3 | HOME ACTIVITIES | WALK/RUN - PLAYING WITH CHILD(REN) - MODERATE, ONLY ACTIVE PERIODS |
| 102 | 5 | 0.0875 | 370 | 3 | HOME ACTIVITIES | WALK/RUN - PLAYING WITH CHILD(REN) - VIGOROUS, ONLY ACTIVE PERIODS |
| 103 | 3 | 0.0525 | 222 | 3 | HOME ACTIVITIES | CARRYING SMALL CHILDREN |
| 104 | 2 | 0.04375 | 185 | 7 | HOME ACTIVITIES | CHILD CARE-SITTING/KNEELING - DRESSING, BATHING, GROOMING, FEEDING, OCCASIONAL LIFTING OF CHILD-LIGHT EFFORT, GENERAL |
| 105 | 3 | 0.0525 | 222 | 3 | HOME ACTIVITIES | CHILD CARE-STANDING - DRESSING, BATHING, GROOMING, FEEDING, OCCASIONAL LIFTING OF CHILD-LIGHT EFFORT |
| 106 | 4 | 0.07 | 296 | 3 | HOME ACTIVITIES | ELDER CARE, DISABLED ADULT, ONLY ACTIVE PERIODS |
| 107 | 2 | 0.02625 | 111 | 7 | HOME ACTIVITIES | RECLINING WITH BABY |
| 108 | 2 | 0.04375 | 185 | 7 | HOME ACTIVITIES | SIT, PLAYING WITH ANIMALS, LIGHT, ONLY ACTIVE PERIODS |
| 109 | 3 | 0.049 | 207 | 3 | HOME ACTIVITIES | STAND, PLAYING WITH ANIMALS, LIGHT, ONLY ACTIVE PERIODS |
| 110 | 3 | 0.049 | 207 | 3 | HOME ACTIVITIES | WALK/RUN, PLAYING WITH ANIMALS, LIGHT, ONLY ACTIVE PERIODS |
| 111 | 4 | 0.07 | 296 | 3 | HOME ACTIVITIES | WALK/RUN, PLAYING WITH ANIMALS, MODERATE, ONLY ACTIVE PERIODS |
| 112 | 5 | 0.0875 | 370 | 3 | HOME ACTIVITIES | WALK/RUN, PLAYING WITH ANIMALS, VIGOROUS, ONLY ACTIVE PERIODS |
| 113 | 4 | 0.06125 | 259 | 3 | HOME ACTIVITIES | STANDING - BATHING DOG |
| 114 | 3 | 0.0525 | 222 | 3 | HOME REPAIR | AIRPLANE REPAIR |
| 115 | 4 | 0.07 | 296 | 3 | HOME REPAIR | AUTOMOBILE BODY WORK |
| 116 | 3 | 0.0525 | 222 | 3 | HOME REPAIR | AUTOMOBILE REPAIR |
| 117 | 3 | 0.0525 | 222 | 3 | HOME REPAIR | CARPENTRY, GENERAL, WORKSHOP |
| 118 | 6 | 0.105 | 444 | 3 | HOME REPAIR | CARPENTRY, OUTSIDE HOUSE, INSTALLING RAIN GUTTERS, BUILDING A FENCE |
| 119 | 4 | 0.07875 | 333 | 3 | HOME REPAIR | CARPENTRY, FINISHING OR REFINISHING CABINETS OR FURNITURE |
| 120 | 8 | 0.13125 | 555 | 3 | HOME REPAIR | CARPENTRY, SAWING HARDWOOD |
| 121 | 5 | 0.0875 | 370 | 3 | HOME REPAIR | CAULKING, CHINKING LOG CABIN |
| 122 | 4 | 0.07875 | 333 | 3 | HOME REPAIR | CAULKING, EXCEPT LOG CABIN |
| 123 | 5 | 0.0875 | 370 | 3 | HOME REPAIR | CLEANING GUTTERS |
| 124 | 5 | 0.0875 | 370 | 3 | HOME REPAIR | EXCAVATING GARAGE |
| 125 | 5 | 0.0875 | 370 | 3 | HOME REPAIR | HANGING STORM WINDOWS |
| 126 | 4 | 0.07875 | 333 | 3 | HOME REPAIR | LAYING OR REMOVING CARPET |

FIG. 8D    TO FIG. 8E

FROM FIG. 8D

| | | | | |
|---|---|---|---|---|
| 127 | 4 | 0.07875 | 333 | HOME REPAIR | LAYING TILE OR LINOLEUM, REPAIRING APPLIANCES |
| 128 | 5 | 0.0875 | 370 | HOME REPAIR | PAINTING, OUTSIDE HOME |
| 129 | 3 | 0.0525 | 222 | HOME REPAIR | PAINTING, PAPERING, PLASTERING, SCRAPING, INSIDE HOUSE, HANGING SHEET ROCK, REMODELING |
| 130 | 4 | 0.07875 | 333 | HOME REPAIR | PAINTING |
| 131 | 3 | 0.0525 | 222 | HOME REPAIR | PUT ON AND REMOVAL OF TARP - SAILBOAT |
| 132 | 6 | 0.105 | 444 | HOME REPAIR | ROOFING |
| 133 | 4 | 0.07875 | 333 | HOME REPAIR | SANDING FLOORS WITH A POWER SANDER |
| 134 | 4 | 0.07875 | 333 | HOME REPAIR | SCRAPING AND PAINTING SAILBOAT OR POWERBOAT |
| 135 | 5 | 0.0875 | 370 | HOME REPAIR | SPREADING DIRT WITH A SHOVEL |
| 136 | 4 | 0.07875 | 333 | HOME REPAIR | WASHING AND WAXING HULL OF SAILBOAT, CAR, POWERBOAT, AIRPLANE |
| 137 | 4 | 0.07875 | 333 | HOME REPAIR | WASHING FENCE, PAINTING FENCE |
| 138 | 3 | 0.0525 | 222 | HOME REPAIR | WIRING, PLUMBING |
| 139 | 1 | 0.0175 | 74 | INACTIVITY | QUIET LYING QUIETLY, WATCHING TELEVISION |
| 140 | 1 | 0.0175 | 74 | INACTIVITY | QUIET LYING QUIETLY, DOING NOTHING, LYING IN BED AWAKE, LISTENING TO MUSIC (NOT TALKING OR READING) |
| 141 | 1 | 0.0175 | 74 | INACTIVITY | QUIET SITTING QUIETLY AND WATCHING TELEVISION |
| 142 | 1 | 0.0175 | 74 | INACTIVITY | QUIET SITTING QUIETLY, SITTING SMOKING, LISTENING TO MUSIC (NOT TALKING OR READING), WATCHING A MOVIE IN A THEATER |
| 143 | 0.9 | 0.01575 | 67 | INACTIVITY | QUIET SLEEPING |
| 144 | 1 | 0.021 | 89 | INACTIVITY | QUIET STANDING QUIETLY (STANDING IN A LINE) |
| 145 | 1 | 0.0175 | 74 | INACTIVITY | LIGHT RECLINING - WRITING |
| 146 | 1 | 0.0175 | 74 | INACTIVITY | LIGHT RECLINING - TALKING OR TALKING ON PHONE |
| 147 | 1 | 0.0175 | 74 | INACTIVITY | LIGHT RECLINING - READING |
| 148 | 1 | 0.0175 | 74 | INACTIVITY | LIGHT MEDITATING |
| 149 | 5 | 0.0875 | 370 | YARD WORK | CARRYING, LOADING OR STACKING WOOD, LOADING/UNLOADING OR CARRYING LUMBER |
| 150 | 6 | 0.0105 | 444 | YARD WORK | CHOPPING WOOD, SPLITTING LOGS |
| 151 | 5 | 0.0875 | 370 | YARD WORK | CLEARING LAND, HAULING BRANCHES, WHEELBARROW CHORES |
| 152 | 5 | 0.0875 | 370 | YARD WORK | DIGGING SANDBOX |
| 153 | 5 | 0.0875 | 370 | YARD WORK | DIGGING, SPADING, FILLING GARDEN, COMPOSTING |
| 154 | 6 | 0.105 | 444 | YARD WORK | GARDENING WITH HEAVY POWER TOOLS, TILLING A GARDEN, CHAIN SAW |
| 155 | 5 | 0.0875 | 370 | YARD WORK | LAYING CRUSHED ROCK |
| 156 | 5 | 0.0875 | 370 | YARD WORK | LAYING SOD |
| 157 | 6 | 0.09625 | 407 | YARD WORK | MOWING LAWN, GENERAL |

FIG. 8E  TO FIG. 8F

FROM FIG. 8E

| | | | | | |
|---|---|---|---|---|---|
| 158 | 2 | 0.04375 | 185 | 7 | YARD WORK | MOWING LAWN, RIDING MOWER |
| 159 | 6 | 0.105 | 444 | 3 | YARD WORK | MOWING LAWN, WALK, HAND MOWER |
| 160 | 6 | 0.09625 | 407 | 3 | YARD WORK | MOWING LAWN, WALK, POWER MOWER |
| 161 | 4 | 0.07875 | 333 | 3 | YARD WORK | MOWING LAWN, POWER MOWER |
| 162 | 4 | 0.07875 | 333 | 3 | YARD WORK | OPERATING SNOW BLOWER, WALKING |
| 163 | 4 | 0.07875 | 333 | 3 | YARD WORK | PLANTING SEEDLINGS, SHRUBS |
| 164 | 4 | 0.07875 | 333 | 3 | YARD WORK | PLANTING TREES |
| 165 | 4 | 0.07525 | 318 | 3 | YARD WORK | RAKING LAWN |
| 166 | 4 | 0.07 | 296 | 3 | YARD WORK | RAKING LAWN |
| 167 | 4 | 0.07 | 296 | 3 | YARD WORK | RAKING ROOF WITH SNOW RAKE |
| 168 | 3 | 0.0525 | 222 | 3 | YARD WORK | RIDING SNOW BLOWER |
| 169 | 4 | 0.07 | 296 | 3 | YARD WORK | SACKING GRASS, LEAVES |
| 170 | 6 | 0.105 | 444 | 3 | YARD WORK | SHOVELING SNOW, BY HAND |
| 171 | 4 | 0.07875 | 333 | 3 | YARD WORK | TRIMMING SHRUBS OR TREES, MANUAL CUTTER |
| 172 | 4 | 0.06125 | 259 | 3 | YARD WORK | TRIMMING SHRUBS OR TREES, POWER CUTTER, USING LEAF BLOWER, EDGER |
| 173 | 4 | 0.04375 | 185 | 3 | YARD WORK | WALKING, APPLYING FERTILIZER, OR SEEDING A LAWN |
| 174 | 2 | 0.02625 | 111 | 7 | YARD WORK | WATERING LAWN OR GARDEN, STANDING OR WALKING |
| 175 | 4 | 0.07875 | 333 | 3 | YARD WORK | WEEDING, CULTIVATING GARDEN |
| 176 | 4 | 0.07 | 296 | 3 | YARD WORK | GARDENING, GENERAL |
| 177 | 3 | 0.0525 | 222 | 3 | YARD WORK | PICKING FRUIT OFF TREES, PICKING FRUITS/VEGETABLES, MODERATE EFFORT |
| 178 | 3 | 0.0525 | 222 | 3 | YARD WORK | IMPLIED WALKING/STANDING - PICKING UP YARD, LIGHT, PICKING FLOWERS OR VEGETABLES |
| 179 | 3 | 0.0525 | 222 | 3 | YARD WORK | WALKING, GATHERING GARDENING TOOLS |
| 180 | 2 | 0.02625 | 111 | 7 | MISC. ACTIVITY | SITTING - CARD PLAYING, PLAYING BOARD GAMES |
| 181 | 2 | 0.04025 | 170 | 7 | MISC. ACTIVITY | STANDING - DRAWING (WRITING), CASINO GAMBLING, DUPLICATING MACHINE |
| 182 | 1 | 0.02275 | 96 | 7 | MISC. ACTIVITY | SITTING - READING, BOOK, NEWSPAPER, ETC. |
| 183 | 2 | 0.0315 | 133 | 7 | MISC. ACTIVITY | SITTING - WRITING, DESK WORK, TYPING |
| 184 | 2 | 0.0315 | 133 | 7 | MISC. ACTIVITY | STANDING - TALKING OR TALKING ON THE PHONE |
| 185 | 2 | 0.02625 | 111 | 7 | MISC. ACTIVITY | SITTING - TALKING OR TALKING ON THE PHONE |
| 186 | 2 | 0.0315 | 133 | 7 | MISC. ACTIVITY | SITTING - STUDYING, GENERAL, INCLUDING READING AND/OR WRITING |
| 187 | 2 | 0.0315 | 133 | 7 | MISC. ACTIVITY | SITTING - IN CLASS, GENERAL, INCLUDING NOTE-TAKING OR CLASS DISCUSSION |
| 188 | 2 | 0.0315 | 133 | 7 | MISC. ACTIVITY | STANDING - READING |

FIG. 8F TO FIG. 8G

FROM FIG. 8F

| # | | | | Category | Description |
|---|---|---|---|---|---|
| 189 | 2 | 0.035 | 148 | MISC. ACTIVITY | STANDING - MISCELLANEOUS |
| 190 | 2 | 0.02625 | 111 | MISC. ACTIVITY | SITTING - ARTS AND CRAFTS, LIGHT EFFORT |
| 191 | 2 | 0.035 | 148 | MISC. ACTIVITY | SITTING - ARTS AND CRAFTS, MODERATE EFFORT |
| 192 | 2 | 0.0315 | 133 | MISC. ACTIVITY | STANDING - ARTS AND CRAFTS, LIGHT EFFORT |
| 193 | 3 | 0.0525 | 222 | MISC. ACTIVITY | STANDING - ARTS AND CRAFTS, MODERATE EFFORT |
| 194 | 4 | 0.06125 | 259 | MISC. ACTIVITY | STANDING - ARTS AND CRAFTS, VIGOROUS EFFORT |
| 195 | 2 | 0.02625 | 111 | MISC. ACTIVITY | RETREAT/FAMILY REUNION ACTIVITIES INVOLVING SITTING, RELAXING, TALKING, EATING |
| 196 | 2 | 0.035 | 148 | MISC. ACTIVITY | TOURING/ TRAVELING/ VACATION INVOLVING WALKING AND RIDING |
| 197 | 2 | 0.04375 | 185 | MISC. ACTIVITY | CAMPING INVOLVING STANDING, WALKING, SITTING, LIGHT-TO-MODERATE EFFORT |
| 198 | 2 | 0.02625 | 111 | MISC. ACTIVITY | SITTING AT A SPORTING EVENT, SPECTATOR |
| 199 | 2 | 0.0315 | 133 | MUSIC PLAYING | ACCORDION |
| 200 | 2 | 0.035 | 148 | MUSIC PLAYING | CELLO |
| 201 | 2 | 0.04375 | 185 | MUSIC PLAYING | CONDUCTING |
| 202 | 4 | 0.07 | 296 | MUSIC PLAYING | DRUMS |
| 203 | 2 | 0.035 | 148 | MUSIC PLAYING | FLUTE (SITTING) |
| 204 | 2 | 0.035 | 148 | MUSIC PLAYING | HORN |
| 205 | 2 | 0.04375 | 185 | MUSIC PLAYING | PIANO OR ORGAN |
| 206 | 4 | 0.06125 | 259 | MUSIC PLAYING | TROMBONE |
| 207 | 2 | 0.04375 | 185 | MUSIC PLAYING | TRUMPET |
| 208 | 2 | 0.04375 | 185 | MUSIC PLAYING | VIOLIN |
| 209 | 2 | 0.035 | 148 | MUSIC PLAYING | WOODWIND |
| 210 | 2 | 0.035 | 148 | MUSIC PLAYING | GUITAR, CLASSICAL, FOLK (SITTING) |
| 211 | 3 | 0.0525 | 222 | MUSIC PLAYING | GUITAR, ROCK AND ROLL BAND (STANDING) |
| 212 | 4 | 0.07 | 296 | MUSIC PLAYING | MARCHING BAND, PLAYING AN INSTRUMENT, BATON TWIRLING (WALKING) |
| 213 | 4 | 0.06125 | 259 | MUSIC PLAYING | MARCHING BAND, DRUM MAJOR (WALKING) |
| 214 | 4 | 0.07 | 296 | OCCUPATIONAL | BAKERY, GENERAL, MODERATE EFFORT |
| 215 | 2 | 0.04375 | 185 | OCCUPATIONAL | BAKERY, LIGHT EFFORT |
| 216 | 2 | 0.04025 | 170 | OCCUPATIONAL | BOOKBINDING |
| 217 | 6 | 0.105 | 444 | OCCUPATIONAL | BUILDING ROAD (INCLUDING HAULING DEBRIS, DRIVING HEAVY MACHINERY) |
| 218 | 2 | 0.035 | 148 | OCCUPATIONAL | BUILDING ROAD, DIRECTING TRAFFIC (STANDING) |
| 219 | 4 | 0.06125 | 259 | OCCUPATIONAL | CARPENTRY, GENERAL |

FIG. 8G TO FIG. 8H

FROM FIG. 8G

| | | | | |
|---|---|---|---|---|
| 220 | 8 | 0.014 | 592 | 3 | OCCUPATIONAL | CARRYING HEAVY LOADS, SUCH AS BRICKS |
| 221 | 8 | 0.014 | 592 | 3 | OCCUPATIONAL | CARRYING MODERATE LOADS UP STAIRS, MOVING BOXES (15-40 POUNDS) |
| 222 | 2 | 0.04375 | 185 | 7 | OCCUPATIONAL | CHAMBERMAID, MAKING BED (NURSING) |
| 223 | 6 | 0.11375 | 481 | 3 | OCCUPATIONAL | COAL MINING, DRILLING COAL, ROCK |
| 224 | 6 | 0.11375 | 481 | 3 | OCCUPATIONAL | COAL MINING, ERECTING SUPPORTS |
| 225 | 6 | 0.105 | 444 | 3 | OCCUPATIONAL | COAL MINING, GENERAL |
| 226 | 7 | 0.1225 | 518 | 3 | OCCUPATIONAL | COAL MINING, SHOVELING COAL |
| 227 | 6 | 0.09625 | 407 | 3 | OCCUPATIONAL | CONSTRUCTION, OUTSIDE, REMODELING |
| 228 | 3 | 0.0525 | 222 | 3 | OCCUPATIONAL | CUSTODIAL WORK - BUFFING THE FLOOR WITH ELECTRIC BUFFER |
| 229 | 2 | 0.04375 | 185 | 7 | OCCUPATIONAL | CUSTODIAL WORK - CLEANING SINK AND TOILET, LIGHT EFFORT |
| 230 | 2 | 0.04375 | 185 | 7 | OCCUPATIONAL | CUSTODIAL WORK - DUSTING, LIGHT EFFORT |
| 231 | 4 | 0.07 | 296 | 3 | OCCUPATIONAL | CUSTODIAL WORK - FEATHERING ARENA FLOOR, MODERATE EFFORT |
| 232 | 4 | 0.06125 | 259 | 3 | OCCUPATIONAL | CUSTODIAL WORK - GENERAL CLEANING, MODERATE EFFORT |
| 233 | 4 | 0.06125 | 259 | 3 | OCCUPATIONAL | CUSTODIAL WORK - MOPPING , MODERATE EFFORT |
| 234 | 3 | 0.0525 | 222 | 3 | OCCUPATIONAL | CUSTODIAL WORK - TAKE OUT TRASH, MODERATE EFFORT |
| 235 | 2 | 0.04375 | 185 | 7 | OCCUPATIONAL | CUSTODIAL WORK - VACUUMING, LIGHT EFFORT |
| 236 | 3 | 0.0525 | 222 | 3 | OCCUPATIONAL | CUSTODIAL WORK - VACUUMING, MODERATE EFFORT |
| 237 | 4 | 0.06125 | 259 | 3 | OCCUPATIONAL | ELECTRICAL WORK, PLUMBING |
| 238 | 8 | 0.14 | 592 | 3 | OCCUPATIONAL | FARMING, BAILING HAY, CLEANING BARN, POULTRY WORK, VIGOROUS EFFORT |
| 239 | 4 | 0.06125 | 259 | 3 | OCCUPATIONAL | FARMING, CHASING CATTLE, NON-STRENUOUS (WALKING0, MODERATE EFFORT |
| 240 | 4 | 0.07 | 296 | 3 | OCCUPATIONAL | FARMING, CHASING CATTLE OR OTHER LIVESTOCK ON HORSEBACK, MODERATE EFFORT |
| 241 | 2 | 0.035 | 148 | 7 | OCCUPATIONAL | FARMING, CHASING CATTLE OR OTHER LIVESTOCK, DRIVING, LIGHT EFFORT |
| 242 | 2 | 0.04375 | 185 | 7 | OCCUPATIONAL | FARMING, DRIVING HARVESTER, CUTTING HAY, IRRIGATION WORK |
| 243 | 2 | 0.04375 | 185 | 7 | OCCUPATIONAL | FARMING, DRIVING TRACTOR |
| 244 | 4 | 0.07 | 296 | 3 | OCCUPATIONAL | FARMING, FEEDING SMALL ANIMALS |
| 245 | 4 | 0.07875 | 333 | 3 | OCCUPATIONAL | FARMING, FEEDING CATTLE, HORSES |
| 246 | 4 | 0.07875 | 333 | 3 | OCCUPATIONAL | FARMING, HAULING WATER FOR ANIMALS, GENERAL HAULING WATER |
| 247 | 6 | 0.105 | 444 | 3 | OCCUPATIONAL | FARMING, TAKING CARE OF ANIMALS (GROOMING, BRUSHING, SHEARING SHEEP, ASSISTING WITH BIRTHING, MEDICAL CARE, BRANDING) |
| 248 | 8 | 0.14 | 592 | 3 | OCCUPATIONAL | FARMING FORKING STRAW BALES, CLEANING CORRAL OR BARN, VIGOROUS EFFORT |
| 249 | 3 | 0.0525 | 222 | 3 | OCCUPATIONAL | FARMING, MILKING BY HAND, MODERATE EFFORT |
| 250 | 2 | 0.02625 | 111 | 7 | OCCUPATIONAL | FARMING, MILKING BY MACHINE, LIGHT EFFORT |

| | | | | | |
|---|---|---|---|---|---|
| 251 | 6 | 0.09625 | 407 | 3 | OCCUPATIONAL | FARMING, SHOVELING GRAIN, MODERATE EFFORT |
| 252 | 12 | 0.21 | 888 | 3 | OCCUPATIONAL | FIRE FIGHTER, GENERAL |
| 253 | 11 | 0.1925 | 814 | 3 | OCCUPATIONAL | FIRE FIGHTER, CLIMBING LADDER WITH FULL GEAR |
| 254 | 8 | 0.14 | 592 | 3 | OCCUPATIONAL | FIRE FIGHTER, HAULING HOSES ON GROUND |
| 255 | 17 | 0.2975 | 1258 | 3 | OCCUPATIONAL | FORESTRY, AX CHOPPING, FAST |
| 256 | 5 | 0.0875 | 370 | 3 | OCCUPATIONAL | FORESTRY, AX CHOPPING, SLOW |
| 257 | 7 | 0.1225 | 518 | 3 | OCCUPATIONAL | FORESTRY, BARKING TREES |
| 258 | 11 | 0.1925 | 814 | 3 | OCCUPATIONAL | FORESTRY, CARRYING LOGS |
| 259 | 8 | 0.14 | 592 | 3 | OCCUPATIONAL | FORESTRY, FELLING TREES |
| 260 | 8 | 0.14 | 592 | 3 | OCCUPATIONAL | FORESTRY, GENERAL |
| 261 | 5 | 0.0875 | 370 | 3 | OCCUPATIONAL | FORESTRY, HOEING |
| 262 | 6 | 0.105 | 444 | 3 | OCCUPATIONAL | FORESTRY, PLANTING BY HAND |
| 263 | 7 | 0.1225 | 518 | 3 | OCCUPATIONAL | FORESTRY, SAWING BY HAND |
| 264 | 4 | 0.07875 | 333 | 3 | OCCUPATIONAL | FORESTRY, SAWING, POWER |
| 265 | 9 | 0.1575 | 666 | 3 | OCCUPATIONAL | FORESTRY, TRIMMING TREES |
| 266 | 4 | 0.07 | 296 | 3 | OCCUPATIONAL | FORESTRY, WEEDING |
| 267 | 4 | 0.07875 | 333 | 3 | OCCUPATIONAL | FURRIER |
| 268 | 6 | 0.105 | 444 | 3 | OCCUPATIONAL | HORSE GROOMING |
| 269 | 8 | 0.14 | 592 | 3 | OCCUPATIONAL | HORSE RACING, GALLOPING |
| 270 | 6 | 0.11375 | 481 | 3 | OCCUPATIONAL | HORSE RACING, TROTTING |
| 271 | 3 | 0.0455 | 192 | 3 | OCCUPATIONAL | HORSE RACING, WALKING |
| 272 | 4 | 0.06125 | 259 | 7 | OCCUPATIONAL | LOCKSMITH |
| 273 | 2 | 0.04375 | 185 | 3 | OCCUPATIONAL | MACHINE TOOLING, MACHINING, WORKING SHEET METAL |
| 274 | 3 | 0.0525 | 222 | 3 | OCCUPATIONAL | MACHINE TOOLING, OPERATING LATHE |
| 275 | 5 | 0.0875 | 370 | 3 | OCCUPATIONAL | MACHINE TOOLING, OPERATING PUNCH PRESS |
| 276 | 4 | 0.07 | 296 | 3 | OCCUPATIONAL | MACHINE TOOLING, TAPPING AND DRILLING |
| 277 | 3 | 0.0525 | 222 | 3 | OCCUPATIONAL | MACHINE TOOLING, WELDING |
| 278 | 7 | 0.1225 | 518 | 3 | OCCUPATIONAL | MASONRY, CONCRETE |
| 279 | 4 | 0.07 | 296 | 3 | OCCUPATIONAL | MASSEUR, MASSEUSE (STANDING) |
| 280 | 8 | 0.13125 | 555 | 3 | OCCUPATIONAL | MOVING, PUSHING HEAVY OBJECTS, 75 LBS OR MORE (DESKS, MOVING VAN WORK) |
| 281 | 12 | 0.21 | 888 | 3 | OCCUPATIONAL | SKINDIVING OR SCUBA DIVING AS A FROGMAN (NAVY SEAL) |

FROM FIG. 8H / TO FIG. 8J

FROM FIG. 8I

| # | | | | |
|---|---|---|---|---|
| 282 | 2 | 0.04375 | 185 | 7 OCCUPATIONAL | OPERATING HEAVY DUTY EQUIPMENT/AUTOMATED, NOT DRIVING |
| 283 | 4 | 0.07875 | 333 | 3 OCCUPATIONAL | ORANGE GROVE WORK |
| 284 | 2 | 0.04025 | 170 | 7 OCCUPATIONAL | PRINTING (STANDING) |
| 285 | 2 | 0.04375 | 185 | 7 OCCUPATIONAL | POLICE, DIRECTING TRAFFIC (STANDING) |
| 286 | 2 | 0.035 | 148 | 7 OCCUPATIONAL | POLICE, DRIVING A SQUAD CAR (SITTING) |
| 287 | 1 | 0.02275 | 96 | 3 OCCUPATIONAL | POLICE, RIDING IN A SQUAD CAR (SITTING) |
| 288 | 4 | 0.07 | 296 | 7 OCCUPATIONAL | POLICE, MAKING AN ARREST (STANDING) |
| 289 | 2 | 0.04375 | 185 | 3 OCCUPATIONAL | SHOE REPAIR, GENERAL |
| 290 | 8 | 0.14875 | 629 | 3 OCCUPATIONAL | SHOVELING, DIGGING DITCHES |
| 291 | 9 | 0.15750 | 666 | 3 OCCUPATIONAL | SHOVELING, HEAVY (MORE THAN 16 POUNDS/MINUTE) |
| 292 | 6 | 0.105 | 444 | 3 OCCUPATIONAL | SHOVELING, LIGHT (LESS THAN 10 POUNDS/MINUTE) |
| 293 | 7 | 0.1225 | 518 | 3 OCCUPATIONAL | SHOVELING, MODERATE (10-15 POUNDS/MINUTE) |
| 294 | 2 | 0.02625 | 111 | 7 OCCUPATIONAL | SITTING-LIGHT OFFICE WORK, GENERAL (CHEMISTRY LAB WORK, LIGHT USE OF HAND TOOLS, WATCH REPAIR OR MICRO-ASSEMBLY, LIGHT ASSEMBLY/REPAIR) |
| 295 | 2 | 0.02625 | 111 | 7 OCCUPATIONAL | SITTING MEETINGS, GENERAL, AND/OR WITH TALKING INVOLVED, EATING AT A BUSINESS MEETING |
| 296 | 2 | 0.04375 | 185 | 7 OCCUPATIONAL | SITTING - MODERATE (HEAVY LEVERS, RIDING MOWER/FORKLIFT, CRANE OPERATION), TEACHING STRETCHING OR YOGA |
| 297 | 2 | 0.4025 | 170 | 7 OCCUPATIONAL | STANDING-LIGHT (BARTENDING, STORE CLERK, ASSEMBLING, FILING, DUPLICATING, PUTTING UP A CHRISTMAS TREE), STANDING AND TALKING AT WORK, CL |
| 298 | 3 | 0.0525 | 222 | 3 OCCUPATIONAL | STANDING-LIGHT/MODERATE (ASSEMBLE/REPAIR HEAVY PARTS, WELDING, STOCKING, AUTO REPAIR, PACK BOXES FOR MOVING, ETC), PATIENT CARE (A |
| 299 | 4 | 0.07 | 296 | 7 OCCUPATIONAL | LIFTING ITEMS CONTINUOUSLY, 10-20 LBS, WITH LIMITED WALKING OR RESTING |
| 300 | 4 | 0.06125 | 259 | 3 OCCUPATIONAL | STANDING - MODERATE (ASSEMBLING AT FAST RATE, INTERMITTENT, LIFTING 50 LBS, MASONRY, HITCH/TWISTING ROPES |
| 301 | 4 | 0.07 | 296 | 3 OCCUPATIONAL | STANDING - MODERATE/HEAVY (LIFTING MORE THAN 50 LBS, MASONRY, PAINTING, PAPER HANGING) |
| 302 | 5 | 0.0875 | 370 | 3 OCCUPATIONAL | STEEL MILL, FETTLING |
| 303 | 6 | 0.09625 | 407 | 3 OCCUPATIONAL | STEEL MILL, FORGING |
| 304 | 8 | 0.14 | 592 | 3 OCCUPATIONAL | STEEL MILL, HAND ROLLING |
| 305 | 8 | 0.14 | 592 | 3 OCCUPATIONAL | STEEL MILL, MERCHANT MILL ROLLING |
| 306 | 11 | 0.1925 | 814 | 3 OCCUPATIONAL | STEEL MILL, REMOVING SLAG |
| 307 | 8 | 0.13125 | 555 | 3 OCCUPATIONAL | STEEL MILL, TENDING FURNACE |
| 308 | 6 | 0.09625 | 407 | 3 OCCUPATIONAL | STEEL MILL, TIPPING MOLDS |
| 309 | 8 | 0.14 | 592 | 3 OCCUPATIONAL | STEEL MILL, WORKING IN GENERAL |
| 310 | 2 | 0.04375 | 185 | 7 OCCUPATIONAL | TAILORING, CUTTING |
| 311 | 2 | 0.04375 | 185 | 7 OCCUPATIONAL | TAILORING, GENERAL |
| 312 | 2 | 0.035 | 148 | 7 OCCUPATIONAL | TAILORING, HAND SEWING |

FIG. 8J   TO FIG. 8K

FROM FIG. 8J

| | | | | |
|---|---|---|---|---|
| 313 | 0.04375 | 185 | 7 | OCCUPATIONAL | TAILORING, MACHINE SEWING |
| 314 | 0.07 | 296 | 3 | OCCUPATIONAL | TAILORING, PRESSING |
| 315 | 0.06125 | 259 | 3 | OCCUPATIONAL | TAILORING, WEAVING |
| 316 | 0.11375 | 481 | 3 | OCCUPATIONAL | TRUCK DRIVING, LOADING AND UNLOADING TRUCK (STANDING) |
| 317 | 0.02625 | 111 | 6 | OCCUPATIONAL | TYPING, ELECTRIC, MANUAL OR COMPUTER |
| 318 | 0.105 | 444 | 2 | OCCUPATIONAL | USING HEAVY POWER TOOLS SUCH AS PNEUMATIC TOOLS (JACKHAMMERS, DRILLS, ETC.) |
| 319 | 0.14 | 592 | 6 | OCCUPATIONAL | USING HEAVY TOOLS (NOT POWER) SUCH AS SHOVEL, PICK TUNNEL, BAR, SPADE |
| 320 | 0.035 | 148 | 8 | OCCUPATIONAL | WALKING - ON JOB, LESS THAN 2.0 MPH (IN OFFICE OR LAB AREA), VERY SLOW |
| 321 | 0.05775 | 244 | 2 | OCCUPATIONAL | WALKING - ON JOB, 3.0 MPH, IN OFFICE, MODERATE SPEED, NOT CARRYING ANYTHING |
| 322 | 0.0665 | 281 | 3 | OCCUPATIONAL | WALKING - ON JOB 3.5 MPH, IN OFFICE, BRISK SPEED, NOT CARRYING ANYTHING |
| 323 | 0.0525 | 222 | 4 | OCCUPATIONAL | WALKING, 2.5 MPH, SLOWLY AND CARRYING LIGHT OBJECTS LESS THAN 25 POUNDS |
| 324 | 0.0525 | 222 | 3 | OCCUPATIONAL | WALKING, GATHERING THINGS AT WORK, READY TO LEAVE |
| 325 | 0.07 | 296 | 3 | OCCUPATIONAL | WALKING, 3.0 MPH, MODERATELY AND CARRYING LIGHT OBJECTS LESS THAN 25 LBS |
| 326 | 0.07 | 296 | 4 | OCCUPATIONAL | WALKING, PUSHING A WHEELCHAIR |
| 327 | 0.07875 | 333 | 4 | OCCUPATIONAL | WALKING, 3.5 MPH, BRISKLY AND CARRYING OBJECTS LESS THAN 25 POUNDS |
| 328 | 0.0875 | 370 | 5 | OCCUPATIONAL | WALKING - OR WALK DOWNSTAIRS OR STANDING, CARRYING OBJECTS ABOUT 25 TO 49 POUNDS |
| 329 | 0.11375 | 481 | 6 | OCCUPATIONAL | WALKING - OR WALK DOWNSTAIRS OR STANDING, CARRYING OBJECTS ABOUT 50 TO 74 POUNDS |
| 330 | 0.13125 | 555 | 8 | OCCUPATIONAL | WALKING - OR WALK DOWNSTAIRS OR STANDING, CARRYING OBJECTS ABOUT 75 TO 99 POUNDS |
| 331 | 0.14875 | 629 | 8 | OCCUPATIONAL | WALKING - OR WALK DOWNSTAIRS OR STANDING, CARRYING OBJECTS ABOUT 100 POUNDS OR OVER |
| 332 | 0.0525 | 222 | 3 | OCCUPATIONAL | WORKING IN SCENE SHOP, THEATER ACTOR, BACKSTAGE EMPLOYEE |
| 333 | 0.07 | 296 | 4 | OCCUPATIONAL | TEACH PHYSICAL EDUCATION, EXERCISE, SPORTS CLASSES (NON-SPORT PLAY) |
| 334 | 0.11375 | 481 | 6 | OCCUPATIONAL | TEACH PHYSICAL EDUCATION, EXERCISE, SPORTS CLASSES (PARTICIPATE IN THE CLASS) |
| 335 | 0.105 | 444 | 6 | RUNNING | JOG/WALK COMBINATION (JOGGING COMPONENT OF LESS THAN 10 MINUTES |
| 336 | 0.1225 | 518 | 7 | RUNNING | JOGGING, GENERAL |
| 337 | 0.14 | 592 | 8 | RUNNING | JOGGING, IN PLACE |
| 338 | 0.07875 | 333 | 4 | RUNNING | JOGGING ON A MINI-TRAMP |
| 339 | 0.14 | 592 | 8 | RUNNING | RUNNING, 5 MPH (12 MIN/MILE) |
| 340 | 0.1575 | 666 | 9 | RUNNING | RUNNING, 5.2 MPH (11.5 MIN/MILE) |
| 341 | 0.175 | 740 | 10 | RUNNING | RUNNING, 6 MPH (10 MIN/MILE) |
| 342 | 0.1925 | 814 | 11 | RUNNING | RUNNING, 6.7 MPH (9 MIN/MILE) |
| 343 | 0.20125 | 851 | 11 | RUNNING | RUNNING, 7 MPH (8.5 MIN/MILE) |

FIG. 8K  TO FIG. 8L

FROM FIG. 8K

| | | | | | |
|---|---|---|---|---|---|
| 344 | 14 | 0.21875 | 925 | 1 RUNNING | RUNNING, 7.5 MPH (8 MIN/MILE) |
| 345 | 15 | 0.23625 | 999 | 1 RUNNING | RUNNING, 8 MPH (7.5 MIN/MILE) |
| 346 | 16 | 0.245 | 1036 | 1 RUNNING | RUNNING, 8.6 MPH (7 MIN/MILE) |
| 347 | 18 | 0.2625 | 1110 | 1 RUNNING | RUNNING, 9 MPH (6.5 MIN/MILE) |
| 348 | 18 | 0.28 | 1184 | 1 RUNNING | RUNNING, 10 MPH (6 MIN/MILE) |
| 349 | 18 | 0.315 | 1332 | 1 RUNNING | RUNNING, 10.9 MPH (5.5 MIN/MILE) |
| 350 | 9 | 0.1575 | 666 | 1 RUNNING | RUNNING, CROSS COUNTRY |
| 351 | 8 | 0.14 | 592 | 1 RUNNING | GENERAL, RUNNING |
| 352 | 8 | 0.14 | 592 | 1 RUNNING | RUNNING, IN PLACE |
| 353 | 15 | 0.2625 | 1110 | 1 RUNNING | RUNNING, STAIRS, UP |
| 354 | 10 | 0.175 | 740 | 1 RUNNING | RUNNING, ON A TRACK, TEAM PRACTICE |
| 355 | 8 | 0.14 | 592 | 1 RUNNING | RUNNING, TRAINING, PUSHING A WHEELCHAIR |
| 356 | 3 | 0.0525 | 222 | 1 RUNNING | RUNNING, WHEELING, GENERAL |
| 357 | 2 | 0.035 | 148 | 7 SELF CARE | STANDING - GETTING READY FOR BED, IN GENERAL |
| 358 | 1 | 0.0175 | 74 | 7 SELF CARE | SITTING ON TOILET |
| 359 | 2 | 0.02625 | 111 | 7 SELF CARE | BATHING (SITTING) |
| 360 | 2 | 0.035 | 148 | 7 SELF CARE | DRESSING, UNDRESSING (STANDING OR SITTING) |
| 361 | 2 | 0.02625 | 111 | 7 SELF CARE | EATING (SITTING) |
| 362 | 2 | 0.035 | 148 | 7 SELF CARE | TALKING AND EATING OR EATING ONLY (STANDING) |
| 363 | 1 | 0.0175 | 74 | 7 SELF CARE | TAKING MEDICATION, SITTING OR STANDING |
| 364 | 2 | 0.035 | 148 | 7 SELF CARE | GROOMING (WASHING, SHAVING, BRUSHING TEETH, URINATING, WASHING HANDS, PUTTING ON MAKE-UP), SITTING OR STANDING |
| 365 | 2 | 0.04375 | 185 | 7 SELF CARE | HAIRSTYLING |
| 366 | 1 | 0.0175 | 74 | 7 SELF CARE | HAVING HAIR OR NAILS DONE BY SOMEONE ELSE, SITTING |
| 367 | 2 | 0.035 | 148 | 7 SELF CARE | SHOWERING, TOWELING OFF (STANDING) |
| 368 | 2 | 0.02625 | 111 | 7 SEXUAL ACTIVITY | ACTIVE, VIGOROUS EFFORT |
| 369 | 1 | 0.02275 | 96 | 7 SEXUAL ACTIVITY | GENERAL, MODERATE EFFORT |
| 370 | 1 | 0.0175 | 74 | 7 SEXUAL ACTIVITY | PASSIVE, LIGHT EFFORT, KISSING, HUGGING |
| 371 | 4 | 0.06125 | 259 | 2 ARCHERY | ARCHERY (NON-HUNTING) |
| 372 | 7 | 0.1225 | 518 | 2 BADMINTON | BADMINTON, COMPETITIVE |
| 373 | 4 | 0.07875 | 333 | 2 BADMINTON | BADMINTON, SOCIAL SINGLES AND DOUBLES, GENERAL |
| 374 | 8 | 0.14 | 592 | 2 BASKETBALL | BASKETBALL, GAME |

FIG. 8L  TO FIG. 8M

FROM FIG. 8L

| | | | | | |
|---|---|---|---|---|---|
| 375 | 6 | 0.105 | 444 | 2 | BASKETBALL | BASKETBALL, NON-GAME, GENERAL |
| 376 | 7 | 0.1225 | 518 | 2 | BASKETBALL | BASKETBALL, OFFICIATING |
| 377 | 4 | 0.07875 | 333 | 2 | BASKETBALL | BASKETBALL, SHOOTING BASKETS |
| 378 | 6 | 0.11375 | 481 | 2 | BASKETBALL | BASKETBALL, WHEELCHAIR |
| 379 | 2 | 0.04375 | 185 | 7 | MISC. SPORT | BILLIARDS |
| 380 | 3 | 0.0525 | 222 | 2 | BOWLING | BOWLING |
| 381 | 12 | 0.21 | 888 | 2 | BOXING | BOXING, IN RING, GENERAL |
| 382 | 6 | 0.105 | 444 | 2 | BOXING | BOXING, PUNCHING BAG |
| 383 | 9 | 0.1575 | 666 | 2 | BOXING | BOXING, SPARRING |
| 384 | 7 | 0.1225 | 518 | 2 | MISC. SPORT | BROOMBALL |
| 385 | 5 | 0.0875 | 370 | 2 | MISC. SPORT | CHILDREN'S GAMES (HOPSCOTCH, 4-SQUARE, DODGE BALL, PLAYGROUND APPARATUS, T-BALL, TETHERBALL, MARBLES, JACKS, ACRACE GAMES) |
| 386 | 4 | 0.07 | 296 | 3 | COACHING | COACHING: FOOTBALL, SOCCER, BASKETBALL, BASEBALL, SWIMMING, ETC. |
| 387 | 5 | 0.0875 | 370 | 2 | MISC. SPORT | CRICKET (BATTING, BOWLING) |
| 388 | 2 | 0.04375 | 185 | 7 | MISC. SPORT | CROQUET |
| 389 | 4 | 0.07 | 296 | 2 | MISC. SPORT | CURLING |
| 390 | 2 | 0.04375 | 185 | 7 | MISC. SPORT | DARTS, WALL OR LAWN |
| 392 | 6 | 0.105 | 444 | 2 | MISC. SPORT | FENCING |
| 393 | 9 | 0.1575 | 666 | 2 | FOOTBALL | FOOTBALL, COMPETITIVE |
| 394 | 8 | 0.14 | 592 | 2 | FOOTBALL | FOOTBALL, TOUCH, FLAG, GENERAL |
| 395 | 2 | 0.04375 | 185 | 7 | MISC. SPORT | FOOTBALL OR BASEBALL, PLAYING CATCH |
| 396 | 3 | 0.0525 | 222 | 2 | FRISBEE | FRISBEE PLAYING, GENERAL |
| 397 | 8 | 0.14 | 592 | 2 | FRISBEE | FRISBEE, ULTIMATE |
| 398 | 4 | 0.07875 | 333 | 2 | GOLF | GOLF, GENERAL |
| 399 | 6 | 0.09625 | 407 | 2 | MISC. SPORT | GOLF, CARRYING CLUBS |
| 400 | 4 | 0.07875 | 333 | 2 | GOLF | GOLF, WALKING AND CARRYING CLUBS |
| 401 | 3 | 0.0525 | 222 | 2 | GOLF | GOLF, MINIATURE, DRIVING RANGE |
| 402 | 5 | 0.0875 | 370 | 2 | GOLF | GOLF, PULLING CLUBS |
| 403 | 4 | 0.07525 | 318 | 2 | GOLF | GOLF, WALKING AND PULLING CLUBS |
| 404 | 4 | 0.06125 | 259 | 2 | GOLF | GOLF, USING POWER CART |
| 405 | 4 | 0.07 | 296 | 2 | GYMNASTICS | GYMNASTICS, GENERAL |
| 406 | 4 | 0.07 | 296 | 2 | MISC. SPORT | HACKY SACK |

FIG. 8M  TO FIG. 8N

FROM FIG. 8M

| # | | | | | |
|---|---|---|---|---|---|
| 407 | 12 | 0.21 | 888 | 2 | HANDBALL | HANDBALL, GENERAL |
| 408 | 8 | 0.14 | 592 | 2 | HANDBALL | HANDBALL, TEAM |
| 409 | 4 | 0.06125 | 259 | 2 | MISC. SPORT | HANG GLIDING |
| 410 | 8 | 0.14 | 592 | 2 | HOCKEY | HOCKEY, FIELD |
| 411 | 8 | 0.14 | 592 | 2 | HOCKEY | HOCKEY, ICE |
| 412 | 4 | 0.07 | 296 | 2 | HORSEBACK RIDING | HORSEBACK RIDING, GENERAL |
| 413 | 4 | 0.06125 | 259 | 2 | HORSEBACK RIDING | HORSEBACK RIDING, SADDLING HORSE, GROOMING HORSE |
| 414 | 6 | 0.11375 | 481 | 2 | HORSEBACK RIDING | HORSEBACK RIDING, TROTTING |
| 415 | 2 | 0.04375 | 185 | 7 | HORSEBACK RIDING | HORSEBACK RIDING, WALKING |
| 416 | 3 | 0.0525 | 222 | 2 | MISC. SPORT | HORSESHOE PITCHING, QUOITS |
| 417 | 12 | 0.21 | 888 | 2 | MISC. SPORT | JAI ALAI |
| 418 | 10 | 0.175 | 740 | 2 | MISC. SPORT | JUDO, JUJITSU, KARATE, KICK BOXING, TAE KWAN DO |
| 419 | 4 | 0.07 | 296 | 2 | MISC. SPORT | JUGGLING |
| 420 | 7 | 0.1225 | 518 | 2 | MISC. SPORT | KICKBALL |
| 421 | 8 | 0.14 | 592 | 2 | MISC. SPORT | LACROSSE |
| 422 | 4 | 0.07 | 296 | 2 | MISC. SPORT | MOTOR-CROSS |
| 423 | 9 | 0.1575 | 666 | 2 | MISC. SPORT | ORIENTEERING |
| 424 | 10 | 0.175 | 740 | 2 | PADDLEBALL | PADDLEBALL, COMPETITIVE |
| 425 | 6 | 0.105 | 444 | 2 | PADDLEBALL | PADDLEBALL, CASUAL, GENERAL |
| 426 | 8 | 0.14 | 592 | 2 | MISC. SPORT | POLO |
| 427 | 10 | 0.175 | 740 | 2 | RACQUETBALL | RACQUETBALL, COMPETITIVE |
| 428 | 7 | 0.1225 | 518 | 2 | RACQUETBALL | RACQUETBALL, CASUAL, GENERAL |
| 429 | 11 | 0.1925 | 814 | 2 | ROCK CLIMBING | ROCK CLIMBING, ASCENDING ROCK |
| 430 | 8 | 0.14 | 592 | 2 | ROCK CLIMBING | ROCK CLIMBING, RAPPELLING |
| 431 | 12 | 0.21 | 888 | 1 | ROPE JUMPING | ROPE JUMPING, FAST |
| 432 | 10 | 0.175 | 740 | 1 | ROPE JUMPING | ROPE JUMPING, MODERATE, GENERAL |
| 433 | 8 | 0.14 | 592 | 1 | ROPE JUMPING | ROPE JUMPING, SLOW |
| 434 | 10 | 0.175 | 740 | 2 | MISC. SPORT | RUGBY |
| 435 | 3 | 0.0525 | 222 | 2 | MISC. SPORT | SHUFFLEBOARD, LAWN BOWLING |
| 436 | 5 | 0.0875 | 370 | 2 | MISC. SPORT | SKATEBOARDING |
| 437 | 7 | 0.1225 | 518 | 2 | SKATING | SKATING, ROLLER |

FIG. 8N  TO FIG. 8O

FROM FIG. 8N

| # | | | | | |
|---|---|---|---|---|---|
| 438 | 12 | 0.21 | 888 | 2 SKATING | ROLLER BLADING (IN-LINE SKATING) |
| 439 | 4 | 0.06125 | 259 | 2 MISC. SPORT | SKY DIVING |
| 440 | 10 | 0.175 | 740 | 2 SOCCER | SOCCER, COMPETITIVE |
| 441 | 7 | 0.1225 | 518 | 2 SOCCER | SOCCER, CASUAL, GENERAL |
| 442 | 5 | 0.0875 | 370 | 2 SOFTBALL | SOFTBALL OR BASEBALL, FAST OR SLOW PITCH, GENERAL |
| 443 | 4 | 0.07 | 296 | 2 SOFTBALL | SOFTBALL, OFFICIATING |
| 444 | 6 | 0.105 | 444 | 2 SOFTBALL | SOFTBALL, PITCHING |
| 445 | 12 | 0.21 | 888 | 2 MISC. SPORT | SQUASH |
| 446 | 4 | 0.07 | 296 | 2 MISC. SPORT | TABLE TENNIS, PING PONG |
| 447 | 4 | 0.07 | 296 | 2 MISC. SPORT | TAI CHI |
| 448 | 7 | 0.1225 | 518 | 2 TENNIS | TENNIS, GENERAL |
| 449 | 6 | 0.105 | 444 | 2 TENNIS | TENNIS, DOUBLES |
| 450 | 5 | 0.0875 | 370 | 2 TENNIS | TENNIS, DOUBLES |
| 451 | 8 | 0.14 | 592 | 2 TENNIS | TENNIS, SINGLES |
| 452 | 4 | 0.06125 | 259 | 2 MISC. SPORT | TRAMPOLINE |
| 453 | 4 | 0.07 | 296 | 2 MISC. SPORT | VOLLEYBALL |
| 454 | 8 | 0.14 | 592 | 2 VOLLEYBALL | VOLLEYBALL, COMPETITIVE, IN GYMNASIUM |
| 455 | 3 | 0.0525 | 222 | 2 VOLLEYBALL | VOLLEYBALL, NON-COMPETITIVE, 6 - 9 MEMBER TEAM, GENERAL |
| 456 | 8 | 0.14 | 592 | 2 VOLLEYBALL | VOLLEYBALL, BEACH |
| 457 | 6 | 0.105 | 444 | 2 MISC. SPORT | WRESTLING (ONE MATCH = 5 MINUTES) |
| 458 | 7 | 0.1225 | 518 | 2 MISC. SPORT | WALLYBALL, GENERAL |
| 459 | 4 | 0.07 | 296 | 2 TRACK AND FIELD | TRACK AND FIELD (SHOT, DISCUS, HAMMER THROW) |
| 460 | 6 | 0.105 | 444 | 2 TRACK AND FIELD | TRACK AND FIELD (HIGH JUMP, LONG JUMP, TRIPLE JUMP, JAVELIN, POLE VAULT) |
| 461 | 10 | 0.175 | 740 | 2 TRACK AND FIELD | TRACK AND FIELD (STEEPLECHASE, HURDLES) |
| 462 | 2 | 0.035 | 148 | 7 TRANSPORTATION | AUTOMOBILE OR LIGHT TRUCK (NOT A SEMI) DRIVING |
| 463 | 1 | 0.0175 | 74 | 7 TRANSPORTATION | RIDING IN A CAR OR TRUCK |
| 464 | 1 | 0.0175 | 74 | 7 TRANSPORTATION | RIDING IN A BUS |
| 465 | 2 | 0.035 | 148 | 7 TRANSPORTATION | FLYING AIRPLANE |
| 466 | 2 | 0.04375 | 185 | 7 TRANSPORTATION | MOTOR SCOOTER, MOTORCYCLE |
| 467 | 6 | 0.105 | 444 | 3 TRANSPORTATION | PUSHING PLANE IN AND OUT OF HANGAR |
| 468 | 3 | 0.0525 | 222 | 3 TRANSPORTATION | DRIVING HEAVY TRUCK, TRACTOR, BUS |

FIG. 8O    TO FIG. 8P

FROM FIG. 8O

| | | | | | |
|---|---|---|---|---|---|
| 469 | 0.1225 | 7 | 518 | | WALKING | BACKPACKING |
| 470 | 0.06125 | 4 | 259 | | WALKING | CARRYING INFANT OR 15 POUND LOAD (E.G. SUITCASE), LEVEL GROUND OR DOWNSTAIRS |
| 471 | 0.1575 | 9 | 666 | | WALKING | CARRYING LOAD UPSTAIRS, GENERAL |
| 472 | 0.0875 | 5 | 370 | | WALKING | CARRYING 1 TO 15 lb LOAD, UPSTAIRS |
| 473 | 0.105 | 6 | 444 | | WALKING | CARRYING 16-24 lb LOAD, UPSTAIRS |
| 474 | 0.14 | 8 | 592 | | WALKING | CARRYING 25-49 lb LOAD, UPSTAIRS |
| 475 | 0.175 | 10 | 740 | | WALKING | CARRYING 50-74 lb LOAD, UPSTAIRS |
| 476 | 0.21 | 12 | 888 | | WALKING | CARRYING 74+ lb LOAD, UPSTAIRS |
| 477 | 0.0525 | 3 | 222 | | WALKING | LOADING/UNLOADING A CAR |
| 478 | 0.1225 | 7 | 518 | | WALKING | CLIMBING HILLS WITH 0 TO 9 POUND LOAD |
| 479 | 0.13125 | 8 | 555 | | WALKING | CLIMBING HILLS WITH 10 TO 20 POUND LOAD |
| 480 | 0.14 | 8 | 592 | | WALKING | CLIMBING HILLS WITH 21 TO 42 POUND LOAD |
| 481 | 0.1575 | 9 | 666 | | WALKING | CLIMBING HILLS WITH 42+ POUND LOAD |
| 482 | 0.0525 | 3 | 222 | | WALKING | DOWNSTAIRS |
| 483 | 0.105 | 6 | 444 | | WALKING | HIKING, CROSS COUNTRY |
| 484 | 0.04375 | 2 | 185 | | WALKING | BIRD WATCHING |
| 485 | 0.11375 | 6 | 481 | 7 | WALKING | MARCHING, RAPIDLY, MILITARY |
| 486 | 0.04375 | 2 | 185 | 7 | WALKING | PUSHING OR PULLING STROLLER WITH CHILD OR WALKING WITH CHILDREN |
| 487 | 0.07 | 4 | 296 | | WALKING | PUSHING A WHEELCHAIR, NON-OCCUPATIONAL SETTING |
| 488 | 0.11375 | 6 | 481 | | WALKING | RACE WALKING |
| 489 | 0.14 | 8 | 592 | | WALKING | ROCK OR MOUNTAIN CLIMBING |
| 490 | 0.14 | 8 | 592 | | WALKING | UP STAIRS, USING OR CLIMBING UP LADDER |
| 491 | 0.0875 | 5 | 370 | | WALKING | USING CRUTCHES |
| 492 | 0.035 | 2 | 148 | 7 | WALKING | WALKING, HOUSEHOLD WALKING |
| 493 | 0.035 | 2 | 148 | 7 | WALKING | WALKING, LESS THAN 2.0 mph, LEVEL GROUND, STROLLING, VERY SLOW |
| 494 | 0.04375 | 2 | 185 | 7 | WALKING | WALKING, 2.0 mph, LEVEL, SLOW PACE, FIRM SURFACE |
| 495 | 0.06125 | 4 | 259 | | WALKING | WALKING FOR PLEASURE |
| 496 | 0.04375 | 2 | 185 | 7 | WALKING | WALKING FROM HOUSE TO CAR OR BUS, FROM CAR OR BUS TO GO PLACES, FROM CAR OR BUS TO AND FROM THE WORKSITE |
| 497 | 0.04375 | 2 | 185 | 7 | WALKING | WALKING TO NEIGHBOR'S HOUSE OR FAMILY'S HOUSE FOR SOCIAL REASONS |
| 498 | 0.0525 | 3 | 222 | | WALKING | WALKING THE DOG |
| 499 | 0.0525 | 3 | 222 | 1 | WALKING | WALKING, 2.5 mph FIRM SURFACE |

FIG. 8P    TO FIG. 8Q

FROM FIG. 8P

| | | | | | |
|---|---|---|---|---|---|
| 500 | 3 | 0.049 | 207 | 1 WALKING | WALKING, 2.5 mph, DOWNHILL |
| 501 | 3 | 0.05775 | 244 | 1 WALKING | WALKING, 3.0 mph, LEVEL, MODERATE PACE, FIRM SURFACE |
| 502 | 4 | 0.0665 | 281 | 1 WALKING | WALKING, 3.5 mph, LEVEL, BRISK, FIRM SURFACE, WALKING FOR EXERCISE |
| 503 | 6 | 0.105 | 444 | 1 WALKING | WALKING, 3.5 mph, UPHILL |
| 504 | 5 | 0.0875 | 370 | 1 WALKING | WALKING, 4.0 mph, LEVEL, FIRM SURFACE, VERY BRISK PACE |
| 505 | 6 | 0.11025 | 466 | 1 WALKING | WALKING, 4.5 mph, LEVEL, FIRM SURFACE, VERY, VERY BRISK |
| 506 | 8 | 0.14 | 592 | 1 WALKING | WALKING, 5.0 mph |
| 507 | 4 | 0.06125 | 259 | 1 WALKING | WALKING, FOR PLEASURE, WORK BREAK |
| 508 | 5 | 0.0875 | 370 | 1 WALKING | WALKING, GRASS TRACK |
| 509 | 4 | 0.07 | 296 | 1 WALKING | WALKING, TO WORK OR CLASS |
| 510 | 2 | 0.04375 | 185 | 1 WALKING | WALKING, TO AND FROM AN OUTHOUSE |
| 511 | 2 | 0.04375 | 185 | 7 WATER ACTIVITIES | BOATING, POWER |
| 512 | 4 | 0.07 | 296 | 2 WATER ACTIVITIES | CANOEING, ON CAMPING TRIP |
| 513 | 3 | 0.05775 | 244 | 2 WATER ACTIVITIES | CANOEING, HARVESTING WILD RICE, KNOCKING RICE OFF THE STALKS |
| 514 | 7 | 0.1225 | 518 | 2 WATER ACTIVITIES | CANOEING, PORTAGING |
| 515 | 3 | 0.0525 | 222 | 2 WATER ACTIVITIES | CANOEING, ROWING, 2.0-3.9 mph, LIGHT EFFORT |
| 516 | 7 | 0.1225 | 518 | 2 WATER ACTIVITIES | CANOEING, ROWING, 4.0-5.9 mph, MODERATE EFFORT |
| 517 | 12 | 0.21 | 888 | 2 WATER ACTIVITIES | CANOEING, ROWING, >6 mph, VIGOROUS EFFORT |
| 518 | 4 | 0.06125 | 259 | 2 WATER ACTIVITIES | CANOEING, ROWING, FOR PLEASURE, GENERAL |
| 519 | 12 | 0.21 | 888 | 2 WATER ACTIVITIES | CANOEING, ROWING, IN COMPETITION, OR CREW OR SCULLING |
| 520 | 3 | 0.0525 | 222 | 2 WATER ACTIVITIES | DIVING, SPRINGBOARD OR PLATFORM |
| 521 | 5 | 0.0875 | 370 | 2 WATER ACTIVITIES | KAYAKING |
| 522 | 4 | 0.07 | 296 | 2 WATER ACTIVITIES | PADDLE BOAT |
| 523 | 3 | 0.0525 | 222 | 2 WATER ACTIVITIES | SAILING, BOAT AND BOARD SAILING, WINDSURFING, ICE SAILING, GENERAL |
| 524 | 5 | 0.0875 | 370 | 2 WATER ACTIVITIES | SAILING, IN COMPETITION |
| 525 | 3 | 0.0525 | 222 | 2 WATER ACTIVITIES | SAILING, SUNFISH/LASER/HOBBY CAT, KEEL BOATS, OCEAN SAILING, YACHTING |
| 526 | 6 | 0.105 | 444 | 2 SKIING | SKIING, WATER |
| 527 | 7 | 0.1225 | 518 | 2 WATER ACTIVITIES | SKIMOBILING |
| 528 | 16 | 0.28 | 1184 | 2 WATER ACTIVITIES | SKINDIVING, FAST |
| 529 | 12.5 | 0.21875 | 925 | 2 WATER ACTIVITIES | SKINDIVING, MODERATE |
| 530 | 7 | 0.1225 | 518 | 2 WATER ACTIVITIES | SKINDIVING, SCUBA DIVING, GENERAL |

FIG. 8Q   TO FIG. 8R

FROM FIG. 8Q

| # | | | Category | Description |
|---|---|---|---|---|
| 531 | 5 | 0.0875 | 370 | 2 WATER ACTIVITIES | SNORKELING |
| 532 | 3 | 0.0525 | 222 | 2 WATER ACTIVITIES | SURFING, BODY OR BOARD |
| 533 | 10 | 0.175 | 740 | 1 SWIMMING | SWIMMING LAPS, FREESTYLE, FAST, VIGOROUS EFFORT |
| 534 | 7 | 0.1225 | 518 | 1 SWIMMING | SWIMMING LAPS, FREESTYLE, SLOW, MODERATE OR LIGHT EFFORT |
| 535 | 7 | 0.1225 | 518 | 1 SWIMMING | SWIMMING, BACKSTROKE, GENERAL |
| 536 | 10 | 0.175 | 740 | 1 SWIMMING | SWIMMING, BREASTSTROKE, GENERAL |
| 537 | 11 | 0.1925 | 814 | 1 SWIMMING | SWIMMING, BUTTERFLY, GENERAL |
| 538 | 11 | 0.1925 | 814 | 1 SWIMMING | SWIMMING, CRAWL, FAST (75 YARDS/MINUTE), VIGOROUS EFFORT |
| 539 | 8 | 0.14 | 592 | 1 SWIMMING | SWIMMING, CRAWL, SLOW (50 YARDS/MINUTE), MODERATE OR LIGHT EFFORT |
| 540 | 6 | 0.105 | 444 | 1 SWIMMING | SWIMMING, LAKE, OCEAN, RIVER |
| 541 | 6 | 0.105 | 444 | 1 SWIMMING | SWIMMING, LEISURELY, NOT LAP SWIMMING, GENERAL |
| 542 | 8 | 0.14 | 592 | 1 SWIMMING | SWIMMING, SIDESTROKE, GENERAL |
| 543 | 8 | 0.14 | 592 | 1 SWIMMING | SWIMMING, SYNCHRONIZED |
| 544 | 10 | 0.175 | 740 | 1 SWIMMING | SWIMMING, TREADING WATER, FAST VIGOROUS EFFORT |
| 545 | 4 | 0.07 | 296 | 1 SWIMMING | SWIMMING, TREADING WATER, MODERATE EFFORT, GENERAL |
| 546 | 4 | 0.07 | 296 | 1 GROUP EXERCISE | WATER AEROBICS, WATER CALISTHENICS |
| 547 | 10 | 0.175 | 740 | 2 WATER ACTIVITIES | WATER POLO |
| 548 | 3 | 0.0525 | 222 | 2 WATER ACTIVITIES | WATER VOLLEYBALL |
| 549 | 8 | 0.14 | 592 | 2 WATER ACTIVITIES | WATER JOGGING |
| 550 | 5 | 0.0875 | 370 | 2 WATER ACTIVITIES | WHITEWATER RAFTING, KAYAKING, OR CANOEING |
| 551 | 6 | 0.105 | 444 | 2 WINTER ACTIVITIES | MOVING ICE HOUSE (SET UP/DRILL HOLES, ETC.) |
| 552 | 6 | 0.09625 | 407 | 2 SKATING | SKATING, ICE, 9 MPH OR LESS |
| 553 | 7 | 0.1225 | 518 | 2 SKATING | SKATING, ICE, GENERAL |
| 554 | 9 | 0.1575 | 666 | 2 SKATING | SKATING, ICE, RAPIDLY, MORE THAN 9 MPH |
| 555 | 15 | 0.2625 | 1110 | 2 SKATING | SKATING, SPEED, COMPETITIVE |
| 556 | 7 | 0.1225 | 518 | 2 WINTER ACTIVITIES | SKI JUMPING (CLIMB UP CARRYING SKIS) |
| 557 | 7 | 0.1225 | 518 | 2 SKIING | SKIING, GENERAL |
| 558 | 7 | 0.1225 | 518 | 2 SKIING | SKIING, CROSS COUNTRY, 2.5 MPH, SLOW OR LIGHT EFFORT, SKI WALKING |
| 559 | 8 | 0.14 | 592 | 2 SKIING | SKIING, CROSS COUNTRY, 4.0-4.9 MPH, MODERATE SPEED AND EFFORT, GENERAL |
| 560 | 9 | 0.1575 | 666 | 2 SKIING | SKIING, CROSS COUNTRY, 5.0-7.9 MPH, BRISK SPEED, VIGOROUS EFFORT |
| 561 | 14 | 0.245 | 1036 | 2 SKIING | SKIING, CROSS COUNTRY, >8.0 MPH, RACING |

FIG. 8R  TO FIG. 8S

FROM FIG. 8R

| | | | | | |
|---|---|---|---|---|---|
| 562 | 0.28875 | 1221 | 2 | SKIING | SKIING, CROSS COUNTRY, HARD SNOW, UPHILL, MAXIMUM, SNOW MOUNTAINEERING |
| 563 | 0.0875 | 370 | 2 | SKIING | SKIING, DOWNHILL, LIGHT EFFORT |
| 564 | 0.105 | 444 | 2 | SKIING | SKIING, DOWNHILL, MODERATE EFFORT, GENERAL |
| 565 | 0.14 | 592 | 2 | SKIING | SKIING, DOWNHILL, VIGOROUS EFFORT, RACING |
| 566 | 0.1225 | 518 | 2 | WINTER ACTIVITIES | SLEDDING, TOBOGGANING, BOBSLEDDING, LUGE |
| 567 | 0.14 | 592 | 2 | WINTER ACTIVITIES | SNOW SHOEING |
| 568 | 0.06125 | 259 | 2 | WINTER ACTIVITIES | SNOWMOBILING |
| 569 | 0.175 | 740 | 1 | ELLIPTICAL TRAINER | RUNNING, LIKE VERY FAST RUNNING (6 MINUTE MILES) |
| 570 | 0.14 | 592 | 8 | ELLIPTICAL TRAINER | RUNNING, LIKE FAST RUNNING (7:30 MINUTE MILES) |
| 571 | 0.105 | 444 | 6 | ELLIPTICAL TRAINER | JOGGING, LIKE SLOW-PACED JOGGING (10 MINUTE MILES) |
| 572 | 0.078 | 330 | 4.5 | ELLIPTICAL TRAINER | BRISK, LIKE FAST-PACED WALK |
| 573 | 0.06125 | 259 | 3 | ELLIPTICAL TRAINER | MODERATE, LIKE MODERATE-PACED WALK |
| 574 | 0.04375 | 185 | 2 | ELLIPTICAL TRAINER | LIGHT, LIKE SLOW-PACED WALK |
| 575 | 0.0309 | 131 | 7 | WALKING - TREADMILL | 1 MPH, 0% GRADE |
| 576 | 0.0333 | 141 | 7 | WALKING - TREADMILL | 1 MPH, 1% GRADE |
| 577 | 0.0357 | 151 | 7 | WALKING - TREADMILL | 1 MPH, 2% GRADE |
| 578 | 0.0381 | 161 | 7 | WALKING - TREADMILL | 1 MPH, 3% GRADE |
| 579 | 0.0405 | 171 | 7 | WALKING - TREADMILL | 1 MPH, 4% GRADE |
| 580 | 0.043 | 182 | 7 | WALKING - TREADMILL | 1 MPH, 5% GRADE |
| 581 | 0.0454 | 192 | 7 | WALKING - TREADMILL | 1 MPH, 6% GRADE |
| 582 | 0.0478 | 202 | 1 | WALKING - TREADMILL | 1 MPH, 7% GRADE |
| 583 | 0.0502 | 212 | 1 | WALKING - TREADMILL | 1 MPH, 8% GRADE |
| 584 | 0.0526 | 222 | 1 | WALKING - TREADMILL | 1 MPH, 9% GRADE |
| 585 | 0.055 | 233 | 1 | WALKING - TREADMILL | 1 MPH, 10% GRADE |
| 586 | 0.0443 | 187 | 7 | WALKING - TREADMILL | 2 MPH, 0% GRADE |
| 587 | 0.0491 | 208 | 1 | WALKING - TREADMILL | 2 MPH, 1% GRADE |
| 588 | 0.0539 | 228 | 1 | WALKING - TREADMILL | 2 MPH, 2% GRADE |
| 589 | 0.0588 | 249 | 1 | WALKING - TREADMILL | 2 MPH, 3% GRADE |
| 590 | 0.0636 | 269 | 1 | WALKING - TREADMILL | 2 MPH, 4% GRADE |
| 591 | 0.0684 | 289 | 1 | WALKING - TREADMILL | 2 MPH, 5% GRADE |
| 592 | 0.0732 | 309 | 1 | WALKING - TREADMILL | 2 MPH, 6% GRADE |

FIG. 8S   TO FIG. 8T

| | | | | |
|---|---|---|---|---|
| 593 | 0.0781 | 330 | 1 | WALKING - TREADMILL | 2 MPH, 7% GRADE |
| 594 | 0.0829 | 350 | 1 | WALKING - TREADMILL | 2 MPH, 8% GRADE |
| 595 | 0.0877 | 371 | 1 | WALKING - TREADMILL | 2 MPH, 9% GRADE |
| 596 | 0.0925 | 391 | 1 | WALKING - TREADMILL | 2 MPH, 10% GRADE |
| 597 | 0.0577 | 244 | 1 | WALKING - TREADMILL | 3 MPH, 0% GRADE |
| 598 | 0.0649 | 274 | 1 | WALKING - TREADMILL | 3 MPH, 1% GRADE |
| 599 | 0.0722 | 305 | 1 | WALKING - TREADMILL | 3 MPH, 2% GRADE |
| 600 | 0.0794 | 336 | 1 | WALKING - TREADMILL | 3 MPH, 3% GRADE |
| 601 | 0.0866 | 366 | 1 | WALKING - TREADMILL | 3 MPH, 4% GRADE |
| 602 | 0.0939 | 397 | 1 | WALKING - TREADMILL | 3 MPH, 5% GRADE |
| 603 | 0.1011 | 427 | 1 | WALKING - TREADMILL | 3 MPH, 6% GRADE |
| 604 | 0.1084 | 458 | 1 | WALKING - TREADMILL | 3 MPH, 7% GRADE |
| 605 | 0.1156 | 489 | 1 | WALKING - TREADMILL | 3 MPH, 8% GRADE |
| 606 | 0.1228 | 519 | 1 | WALKING - TREADMILL | 3 MPH, 9% GRADE |
| 607 | 0.1301 | 550 | 1 | WALKING - TREADMILL | 3 MPH, 10% GRADE |
| 608 | 0.0711 | 301 | 1 | WALKING - TREADMILL | 4 MPH, 0% GRADE |
| 609 | 0.0807 | 341 | 1 | WALKING - TREADMILL | 4 MPH, 1% GRADE |
| 610 | 0.0904 | 382 | 1 | WALKING - TREADMILL | 4 MPH, 2% GRADE |
| 611 | 0.1 | 423 | 1 | WALKING - TREADMILL | 4 MPH, 3% GRADE |
| 612 | 0.1097 | 464 | 1 | WALKING - TREADMILL | 4 MPH, 4% GRADE |
| 613 | 0.1193 | 504 | 1 | WALKING - TREADMILL | 4 MPH, 5% GRADE |
| 614 | 0.129 | 545 | 1 | WALKING - TREADMILL | 4 MPH, 6% GRADE |
| 615 | 0.1386 | 586 | 1 | WALKING - TREADMILL | 4 MPH, 7% GRADE |
| 616 | 0.1483 | 627 | 1 | WALKING - TREADMILL | 4 MPH, 8% GRADE |
| 617 | 0.1579 | 667 | 1 | WALKING - TREADMILL | 4 MPH, 9% GRADE |
| 618 | 0.1676 | 708 | 1 | WALKING - TREADMILL | 4 MPH, 10% GRADE |
| 619 | 0.0845 | 357 | 1 | WALKING - TREADMILL | 5 MPH, 0% GRADE |
| 620 | 0.0966 | 408 | 1 | WALKING - TREADMILL | 5 MPH, 1% GRADE |
| 621 | 0.1086 | 459 | 1 | WALKING - TREADMILL | 5 MPH, 2% GRADE |
| 622 | 0.1207 | 510 | 1 | WALKING - TREADMILL | 5 MPH, 3% GRADE |
| 623 | 0.1327 | 561 | 1 | WALKING - TREADMILL | 5 MPH, 4% GRADE |

FIG. 8T

| | | FROM FIG. 8T | | |
|---|---|---|---|---|
| 624 | 0.1448 | 612 | 1 WALKING - TREADMILL | 5 MPH, 5% GRADE |
| 625 | 0.1569 | 663 | 1 WALKING - TREADMILL | 5 MPH, 6% GRADE |
| 626 | 0.1689 | 714 | 1 WALKING - TREADMILL | 5 MPH, 7% GRADE |
| 627 | 0.181 | 765 | 1 WALKING - TREADMILL | 5 MPH, 8% GRADE |
| 628 | 0.193 | 816 | 1 WALKING - TREADMILL | 5 MPH, 9% GRADE |
| 629 | 0.2051 | 867 | 1 WALKING - TREADMILL | 5 MPH, 10% GRADE |
| 630 | 0.1515 | 640 | 1 RUNNING - TREADMILL | 5 MPH, 0% GRADE |
| 631 | 0.1636 | 692 | 1 RUNNING - TREADMILL | 5 MPH, 1% GRADE |
| 632 | 0.1756 | 742 | 1 RUNNING - TREADMILL | 5 MPH, 2% GRADE |
| 633 | 0.1877 | 793 | 1 RUNNING - TREADMILL | 5 MPH, 3% GRADE |
| 634 | 0.1997 | 844 | 1 RUNNING - TREADMILL | 5 MPH, 4% GRADE |
| 635 | 0.2118 | 895 | 1 RUNNING - TREADMILL | 5 MPH, 5% GRADE |
| 636 | 0.2239 | 946 | 1 RUNNING - TREADMILL | 5 MPH, 6% GRADE |
| 637 | 0.2359 | 997 | 1 RUNNING - TREADMILL | 5 MPH, 7% GRADE |
| 638 | 0.248 | 1048 | 1 RUNNING - TREADMILL | 5 MPH, 8% GRADE |
| 639 | 0.26 | 1099 | 1 RUNNING - TREADMILL | 5 MPH, 9% GRADE |
| 640 | 0.2721 | 1150 | 1 RUNNING - TREADMILL | 5 MPH, 10% GRADE |
| 641 | 0.1783 | 754 | 1 RUNNING - TREADMILL | 6 MPH, 0% GRADE |
| 642 | 0.1928 | 815 | 1 RUNNING - TREADMILL | 6 MPH, 1% GRADE |
| 643 | 0.2072 | 876 | 1 RUNNING - TREADMILL | 6 MPH, 2% GRADE |
| 644 | 0.2217 | 937 | 1 RUNNING - TREADMILL | 6 MPH, 3% GRADE |
| 645 | 0.2362 | 998 | 1 RUNNING - TREADMILL | 6 MPH, 4% GRADE |
| 646 | 0.2507 | 1060 | 1 RUNNING - TREADMILL | 6 MPH, 5% GRADE |
| 647 | 0.2651 | 1121 | 1 RUNNING - TREADMILL | 6 MPH, 6% GRADE |
| 648 | 0.2796 | 1182 | 1 RUNNING - TREADMILL | 6 MPH, 7% GRADE |
| 649 | 0.2941 | 1243 | 1 RUNNING - TREADMILL | 6 MPH, 8% GRADE |
| 650 | 0.3085 | 1304 | 1 RUNNING - TREADMILL | 6 MPH, 9% GRADE |
| 651 | 0.323 | 1365 | 1 RUNNING - TREADMILL | 6 MPH, 10% GRADE |
| 652 | 0.2051 | 867 | 1 RUNNING - TREADMILL | 7 MPH, 0% GRADE |
| 653 | 0.222 | 938 | 1 RUNNING - TREADMILL | 7 MPH, 1% GRADE |
| 654 | 0.2389 | 1010 | 1 RUNNING - TREADMILL | 7 MPH, 2% GRADE |

FIG. 8U  TO FIG. 8V

| | | | | |
|---|---|---|---|---|
| 655 | 0.2558 | 1081 | 1 | RUNNING - TREADMILL | 7 MPH, 3% GRADE |
| 656 | 0.2726 | 1152 | 1 | RUNNING - TREADMILL | 7 MPH, 4% GRADE |
| 657 | 0.2895 | 1224 | 1 | RUNNING - TREADMILL | 7 MPH, 5% GRADE |
| 658 | 0.3064 | 1295 | 1 | RUNNING - TREADMILL | 7 MPH, 6% GRADE |
| 659 | 0.3233 | 1367 | 1 | RUNNING - TREADMILL | 7 MPH, 7% GRADE |
| 660 | 0.3402 | 1438 | 1 | RUNNING - TREADMILL | 7 MPH, 8% GRADE |
| 661 | 0.3571 | 1510 | 1 | RUNNING - TREADMILL | 7 MPH, 9% GRADE |
| 662 | 0.3739 | 1581 | 1 | RUNNING - TREADMILL | 7 MPH, 10% GRADE |
| 663 | 0.2319 | 980 | 1 | RUNNING - TREADMILL | 8 MPH, 0% GRADE |
| 664 | 0.2512 | 1062 | 1 | RUNNING - TREADMILL | 8 MPH, 1% GRADE |
| 665 | 0.2705 | 1143 | 1 | RUNNING - TREADMILL | 8 MPH, 2% GRADE |
| 666 | 0.2898 | 1225 | 1 | RUNNING - TREADMILL | 8 MPH, 3% GRADE |
| 667 | 0.3091 | 1307 | 1 | RUNNING - TREADMILL | 8 MPH, 4% GRADE |
| 668 | 0.3284 | 1388 | 1 | RUNNING - TREADMILL | 8 MPH, 5% GRADE |
| 669 | 0.3477 | 1470 | 1 | RUNNING - TREADMILL | 8 MPH, 6% GRADE |
| 670 | 0.367 | 1551 | 1 | RUNNING - TREADMILL | 8 MPH, 7% GRADE |
| 671 | 0.3863 | 1633 | 1 | RUNNING - TREADMILL | 8 MPH, 8% GRADE |
| 672 | 0.2587 | 1094 | 1 | RUNNING - TREADMILL | 9 MPH, 0% GRADE |
| 673 | 0.2804 | 1185 | 1 | RUNNING - TREADMILL | 9 MPH, 1% GRADE |
| 674 | 0.3021 | 1277 | 1 | RUNNING - TREADMILL | 9 MPH, 2% GRADE |
| 675 | 0.3238 | 1369 | 1 | RUNNING - TREADMILL | 9 MPH, 3% GRADE |
| 676 | 0.3455 | 1461 | 1 | RUNNING - TREADMILL | 9 MPH, 4% GRADE |
| 677 | 0.3672 | 1552 | 1 | RUNNING - TREADMILL | 9 MPH, 5% GRADE |
| 678 | 0.3889 | 1644 | 1 | RUNNING - TREADMILL | 9 MPH, 6% GRADE |
| 679 | 0.2855 | 1207 | 1 | RUNNING - TREADMILL | 10 MPH, 0% GRADE |
| 680 | 0.3096 | 1309 | 1 | RUNNING - TREADMILL | 10 MPH, 1% GRADE |
| 681 | 0.3337 | 1411 | 1 | RUNNING - TREADMILL | 10 MPH, 2% GRADE |
| 682 | 0.3579 | 1513 | 1 | RUNNING - TREADMILL | 10 MPH, 3% GRADE |
| 683 | 0.382 | 1615 | 1 | RUNNING - TREADMILL | 10 MPH, 4% GRADE |

FROM FIG. 8U

FIG. 8V

SYSTEM AND METHOD FOR CALCULATING OPTIMAL PERFORMANCE AND WEIGHT CLASSIFICATION

This application is a continuation-in-part of U.S. patent application Ser. No. 10/446,086, filed May 28, 2003 now abandoned by Daniel M. Peplinski, Alan Utter, and David Neiman, which is a continuation-in-part of U.S. patent application Ser. No. 10/355,195, filed Jan. 31, 2003 by Daniel M. Peplinski, Alan Utter, and David Neiman (now U.S. Pat. No. 7,247,023), both of which claim priority to U.S. Provisional Application No. 60/391,587, filed Jun. 27, 2002, and this application claims benefit to those filing dates for priority. This application also claims benefit of U.S. Provisional App. No. 60/826,865, filed Sep. 25, 2006, by Alan Utter, Dave Nieman, and Mark Brittingham, and U.S. Provisional App. No. 60/864,609, filed Nov. 7, 2006, by Alan Utter, Dave Nieman, and Mark Brittingham, and is entitled to those filing dates for priority. The entire contents, including but not limited to the specifications, attachments and drawings, of the above applications are incorporated herein by specific reference.

TECHNICAL FIELD

The present invention relates to a system and method for calculating optimal performance and determining and monitoring weight classifications in conjunction with overall nutrition and activity. More particularly, the present invention relates to a system and method for determining and monitoring weight classifications in conjunction with overall nutrition and activity of individuals of any age and background using the Internet or through software.

BACKGROUND

The problems caused by the overweight condition of students and athletes, as well as adults, is well known, as well as the increasing percentage of overweight individuals at any particular age or grade. A large number of dieting and weight loss methods have been used, but many of these methods encourage or lead to excessive and potentially dangerous weight loss (and gain).

What is needed is an easy-to-use system for calculating optimal performance and determining and monitoring weight classifications in conjunction with overall nutrition and activity of individuals of any age and background, including through the Internet or through software.

SUMMARY OF THE INVENTION

In one exemplary embodiment, the present invention comprises a system and method of conducting a weight, activity and nutritional assessment and monitoring program over a network. The method comprises providing a menu of data entry options, at least one of the data entry options allowing entry of data for an assessment of a subject, determining a weight classification rating, generating a weight plan based on the subject assessment data, the weight plan including a plurality of minimum weights for the subject, each of the minimum weights being associated with a time, and generating a nutritional plan based on the subject data entered.

In one embodiment, a subject is informed of minimum weights that he or she can have at selected time periods. The method also provides a nutrition plan keyed to help the subject honor the weight plan.

According to another embodiment, a method for providing a nutritional plan comprises determining an expected energy expenditure for a subject based at least in part on the subject's activity level, determining a recommended energy intake based on the expected energy expenditure, providing a list of food exchanges for the subject, allowing the subject to select items from the food exchanges, and providing the nutritional plan resulting from the subject's selections.

According to another embodiment, the method comprises generating a weight plan for a subject, which comprises receiving an input of the subject's weight, determining the subject's body fat percentage, calculating a lowest allowable weight-one (allowable weight at a first time period) based at least in part on the subject's body fat percentage, and determining a plurality of minimum weight values based on the lowest allowable weight-one, each weight value being associated with a time.

Additional objects, features and advantages of the invention will be set forth in the description which follows, and in part, will be obvious from the description, or may be learned by practice of the invention. The objects, features and advantages of the invention may be realized and obtained by means of the instrumentalities and combination particularly pointed out in the appended claims.

BRIEF DESCRIPTION OF THE DRAWINGS

FIG. 2 illustrates a method for generating a weight plan in accordance with an exemplary embodiment of the present invention.

FIG. 3 illustrates a method for determining a subject's body composition in accordance with the method shown in FIG. 2.

FIG. 4 illustrates a method for generating a weight plan in accordance with the method shown in FIG. 2.

FIG. 5 is a view of a calculation form in accordance with an exemplary embodiment of the present invention.

FIG. 7 is a view of a students-on-file list in accordance with an exemplary embodiment of the present invention.

FIG. 8 is a view of an activity table in accordance with an exemplary embodiment of the present invention.

DETAILED DESCRIPTION

In accordance with the exemplary embodiments discussed below, a system and methods are disclosed for providing, determining and monitoring weight classifications for individuals of any age and background, including students and athletes, in conjunction with monitoring of overall nutrition and activity.

The system and methods disclosed herein are suitable for people of any age and background. They also are suitable for young individuals, such as students, who are still growing and may not fully understand the harm that may result from being overweight, not receiving proper nutrition, or not engaging in sufficient physical activity.

In one exemplary embodiment, the invention is a computer-based application, and may be accessed through the Internet. The embodiment may comprise an Internet-based system for determining weight classifications for subjects, for providing nutritional information, and for recording and monitoring activity by subjects.

Figure 1:
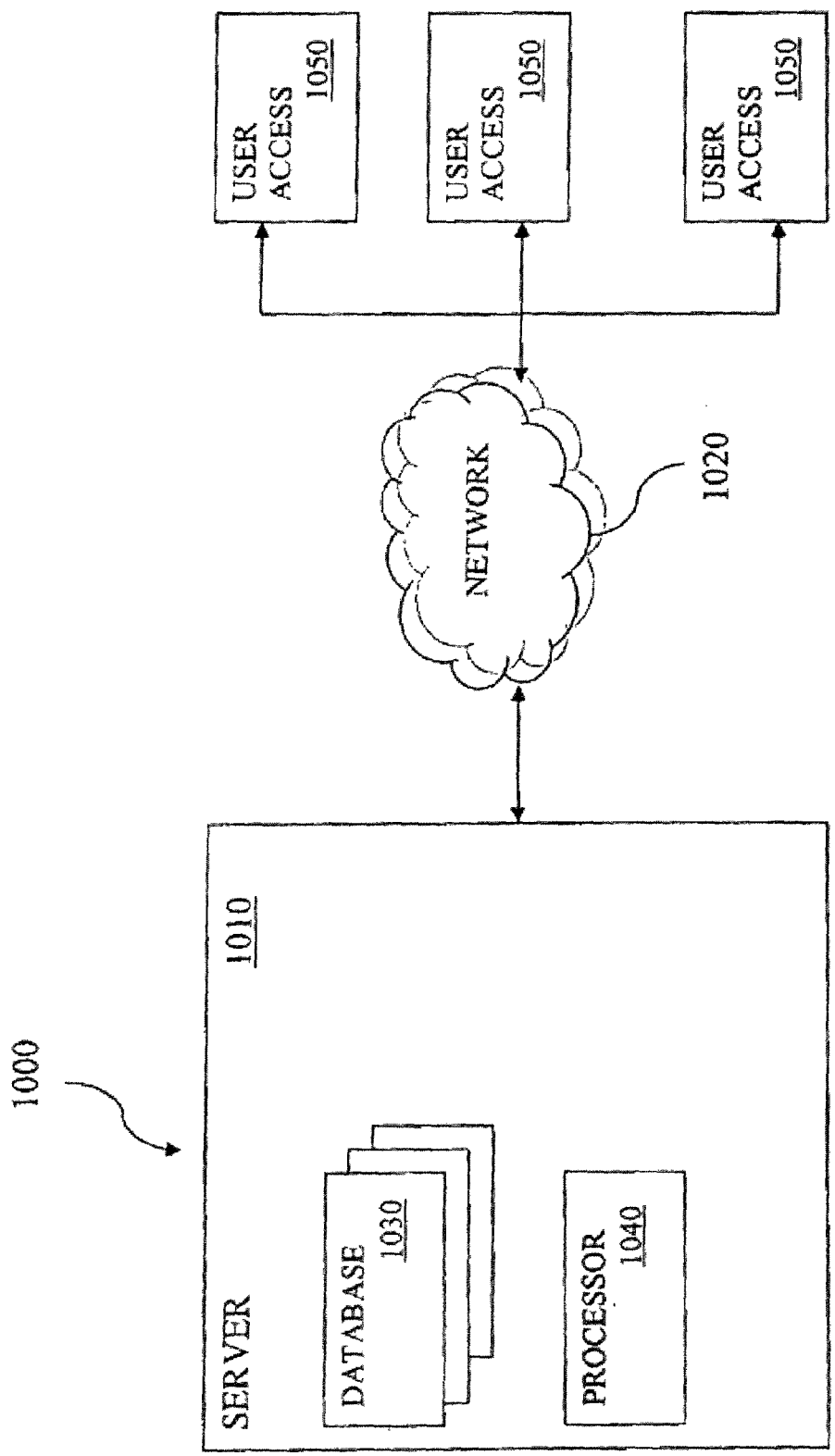
FIG. 1 is a block diagram of an embodiment of a system for providing nutritional and weight information in accordance with an exemplary embodiment of the present invention.
Figure 6:
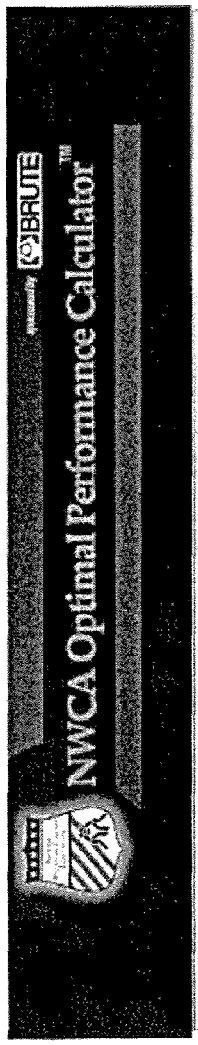
FIG. 6 is a view of a student profile list in accordance with an exemplary embodiment of the present invention.

FIG. 1 is a block diagram of a web-based application of an embodiment of the present invention. The embodiment comprises a computer-based system 1000 for monitoring weight and activity and for providing nutritional information. The system 1000 can perform functions and provide access to users, who need not necessarily be the subject, to information regarding the subject.

In one exemplary embodiment, the system 1000 comprises a server 1010 connected to a network 1020. The server 1010 comprises one or more databases or objects 1030. The databases 1030 can store information relating to weight and nutritional standards, user interface programs, food exchange data, and programs relating to remote access by users such as web browsers and user interface programs.

The network 1020 connects the system 1000 to a plurality of user access ports 1050. The user access ports 1050 can be, for example, a remote computer, a laptop, a personal computer, a workstation or any other processing device located at a site controlled by the user. Alternatively or in addition to the previous embodiment, a user access port 1050 can be located at a site controlled by an owner of the system 1000, and can also be owned by the system 1000 owner. Any number of access ports 1050 can be coupled to the server 1010 on dedicated or non-dedicated access lines.

The network 1020 can be, for example, the Internet, or any other network that allows an exchange of information between a user and the server 1010. In one embodiment, the network 1020 is a dedicated dial-up or local area network (LAN) network. The network 1020 may include hardware such as is known in the art, including an information line, and one or more routers. The information line can be, for example, a telephone line or hardware supporting access via a satellite communication apparatus. The router can be, for example, the Internet backbone.

The server 1010 can be programmed to run and/or access one or more programs in accordance with the methods discussed in this specification. In one embodiment, the server 1010 is programmed to execute a method for classifying a subject for risk for being overweight. In another embodiment, it may be programmed to execute a method for monitoring a subject's weight. The subject can be the user operating at a user access port 1050, or the subject can be a third party whose weight or other data is entered by the user. For example, the user can be the parent and/or physical education instructor of a student, the spouse or trainer of an adult subject, the coach of an athlete participating in organized sports, or a designated assessor. The server 1010 can also be programmed to execute a method for developing a nutritional plan for a subject, as discussed below.

The server 1010 can include a user interface 1060, which may be used to present menus, prompt screens, data displays, and other information to a user at a user access port 1050. The various prompts and screens presented to users by the interface 1060 are discussed in detail below. The user interface 1060 can comprise one or more programs, databases or objects, allowing input by a user and/or transmission of information to the user.

The user access ports 1050 can include any processing devices capable of running a network-interfacing program such as, for example, a web browser. In one exemplary embodiment, the user access port 1050 is a personal computer (PC) programmed with software for communicating with the server 1010. The software can include executable instructions for providing data such as, for example, password and login information for access to the server 1010, formatting information for providing data to the server 1010 in the proper format, or instructions for constructing, for example, prepared forms which may be completed at the user access port 1050 and subsequently forwarded to the server 1010. Alternatively, the server 1010 can include a database of forms that may be completed by a user while the user is in communication with the server 1010 (e.g., while the user is on line). In addition, the user access ports 1050 can have one or more peripherals attached thereto. The user access port 1050 may also be a PC programmed with software to save data generated for prepared forms on computer-readable media, such as (but not limited to) floppy disks, CD-ROMs, and DVDs.

In one exemplary embodiment, a website arrangement may provide for a weight assessment and classification, recommended energy intake, nutritional information, diet and menu plans, and recording and monitoring of activities. The website arrangement can provide such services and information for one or more subjects. In some cases, a user of the website will be a subject, and in other cases the user will be a third party. In yet other cases, the user may be a subject and also a third party with respect to other subjects. A user may have access to some or all of the website. For example, as in the case of a student, the student may only have access to selected portions of the website (i.e., the student is a user), and a third party user, such as a parent or physical education instructor, may have access to that subject's data, as well as data for other subjects (e.g., students).

The exemplary website arrangement is discussed in reference to a student; however, the general principles discussed herein may be applicable to any subject, particularly those for whom weight and nutrition are important. In addition, many aspects of the website can be used by users who are simply interested in weight classification, or in obtaining a nutrition and/or weight loss plan. The website arrangement can be programmed on and executed by the server shown in FIG. 1, or by other server arrangements or configurations. The website arrangement also may be in the form of an executable program stored on a digital medium readable by, for example, a microcomputer, personal computer, laptop computer, or portable computing device.

In one exemplary embodiment, a weight assessment and classification page provides a series of menu options. An instructions menu option can be selected to obtain specific information for using each of the menu options in the website, or for other information relevant to the site. The instructions menu may include, for example, a description of skinfold measurements.

An entering data menu option may be provided to allow a user to input weight assessment and classification data regarding a subject. The subject, as described above, may be the user, who thus may enter his or her own data. The assessments option is used to provide an initial assessment of a subject at the date of the initial assessment or classification. The weight classification data input for a subject includes, but is not limited to, height, weight, body mass index (BMI), triceps skinfold measurements, subscapular skinfold measurements, waist circumference, and percentage of body fat. This data may then used to determine a weight classification for the subject. A plurality of classifications may be used. In one exemplary embodiment, three classifications may be used, as follows: Class 1 for "normal" weight or less than 75% for BMI and body composition; Class 2 for "at risk" for being overweight, or 75% to 90% for BMI and body composition; and Class 3 for being "overweight," or greater than 90% for BMI and body composition.

Input data may also include certain risk factors and medical data. This additional data may be used to screen for medical problems or other concerns.

After inputting the above data and making the initial classification, the data may be saved, and form or report printed. The subject's data is thereby saved in the system.

The energy intake and weight loss plan menu is used to determine a recommended energy intake based on the weight classification. For example, using the three weight classifications given in the exemplary embodiment above, a subject in the normal weight classification would be given a calorie level or range to maintain weight and normal growth. A subject in the at risk for overweight classification would be given a calorie level or range designed to cause the subject to lose a certain amount of weight per week until normal weight is achieved. In one embodiment, this amount may be 0.5 pounds of weight a week. A subject in the overweight classification would be given a calorie level or range to lose another amount (e.g., 1.0 pounds) of weight a week until normal weight is achieved.

The nutritional plan menu option is used to generate a nutritional plan for the subject. A recommended number of food exchanges are provided. A "food exchange" is a selection of food selectable by the subject. The food exchanges may be provided for all food groups, and may be based on the recommended daily energy intake and nutritional guidelines for a healthy diet. A series of prompts may be used to allow the user or subject to a build a suitable menu plan. Menu items may be selected according to the subject's personal likes or dislikes.

The menu monitoring menu option is used to monitor the subject's adherence to the menu plan. The items consumed by the subject are entered into the program on a regular basis, which may be after each meal, or daily.

The activity monitoring menu option is used to monitor the subject's activity levels during a day. Data input includes the amount of time the subject engages in physical exercise or activity, and the amount of time the subject engages in sedentary behavior (e.g., watching TV, working on a computer, playing video games, etc.). This data may be entered into the program on a regular basis, which may be at certain times during the day, or daily.

The weight monitoring menu option is used to monitor some or all of the same measures as used in the initial weight classification and assessment. In one exemplary embodiment, the weight of the subject may be entered on a weekly basis, while height, skinfold measurements, waist circumference, and percent body fat may be entered every three weeks.

In yet another exemplary embodiment, skinfold measurements may be skipped for some individuals, such as adults. In some embodiments, adult subjects may measure waist circumference only.

A method of generating a weight plan will now be discussed with reference to FIGS. 2-4. FIG. 2 is a block diagram of the method for generating a weight plan. In one embodiment, the method is executed by the system 1000 illustrated in FIG. 1. Other apparatuses, however, may be used to employ the method.

In FIG. 2, the step of determining body fat percentage (BF %) and body weight (BW) is disclosed as step 410, in which subject data is entered. The data can be entered on a form such as those discussed below. The subject's body weight BW is preferably measured when the subject is hydrated. The body weight (BW) may therefore be referred to as a "hydrated body weight" or, more generally, a "current weight." This step may also include the entry of raw data such as body caliper measurements used to determine the subject's body fat percentage (BF %). Alternatively, the subject's body fat percentage may be entered directly. Body fat percentage can be provided by, for example, a commercially available service such as BodPod® Other subject data entered at this point can include, but are not limited to, the alpha date, urine specific gravity, subject grade or years in college, and subject name.

In step 420, the subject's body composition is determined. The subject's body composition can include data such as the subject's body density (BD), body fat percentage (BF %), fat weight (FW), and fat free weight (FFW). These values may be displayed on the forms described below. The steps involved in determining the subject's body composition are discussed in detail with reference to FIG. 3 and below.

In step 430, the subject's weight plan is generated. The weight plan can include one or more weight parameters such as, for example, a lowest allowable weight (lowest allowable weight-one, or "LAW 1"). In general terms, LAW 1 can be a lowest recommended weight for a first time period. The weight parameters can also include a lowest allowable weight-two (LAW 2). LAW 2 can be a lowest allowable weight for a subsequent or later time period T2. LAW 2 is typically used to describe a minimum ending weight after a period of weeks. In addition, minimum weights for any number of intermediate time periods, such as weekly time periods, can be calculated. The minimum weights may be used to inform the subject, parents, coaches or others of the minimum weight that the subject should have at any time. Generation of a weight plan is discussed in detail below with reference to FIG. 4.

After the weight plan is generated, the subject's weight may be monitored. In one embodiment, users are capable of monitoring any number of subjects' compliance with prescribed governing body guidelines. The website arrangement described above is particularly advantageous for monitoring the subject's compliance because of the detailed reports available to users. In addition to and alternatively to monitoring by users, the server 1010 may contain a database of subject data, and the subject data can be examined.

FIG. 3 is a block diagram of a method of determining a subject's body composition. The method steps illustrated in FIG. 3 correspond to step 420 in FIG. 2. In step 510, the subject's body density (BD) is determined. Body density may be determined by a number of methods. For example, data from skin-fold measurements may be used to calculate body density. One skin-fold measurement technique involves skin-fold measurements taken in three areas of the body: triceps, subscapular and abdominal. The skin-fold measurements can be entered as subject data in step 410. The median values of each area are then summed, and used in a formula to determine BD. In one exemplary embodiment, the following formula may be used to determine BD: $BD=[1.0982-((SUM\ SF)*0.000815)]+[(SUM\ SF)^2*(0.00000084)]$, where SUM SF is the sum of the skin-fold median values. Alternatively, body density may be measured by known methods such as hydrostatic weighing or commercial devices such as BodPod®, as discussed above.

In step 520, the subject's body fat percentage is calculated. In one exemplary embodiment, body fat percentage (BF %) can be calculated according to the following formula: $BF\%=[(4.57/BD)-4.142]*100$.

In step 530, the subject's fat weight (FW) is calculated. Fat weight is the weight of the fat contained in the subject's body. In one exemplary embodiment, fat weight may be calculated according to the following formula: $FW=BW*(BF\%/100)$.

In step 540, the subject's fat free weight (FFW) is calculated. The fat free weight FFW represents the weight of a subject's body that is comprised of materials other than fat, and may be calculated according to the following formula: $FFW=BW-FW$.

FIG. 4 illustrates a method of determining a weight plan. The steps illustrated in FIG. 4 correspond to step 430 in FIG. 2. In step 610, a lowest allowable weight-one (LAW 1) is calculated. The lowest allowable weight-one is calculated according to the FFW. LAW 1 can be calculated according to:

$$LAW\ 1 = FFW/f$$

In the equation for LAW 1, f is a factor that describes the minimum body fat allowed according to applicable standards (as discussed below).

In step 620, a time period (TIME) is determined. The time period can be described as a period of time between an initial assessment and a "deadline date," and is usually described as a number of discrete time periods of weeks. The deadline date represents a deadline measurement date.

The time period TIME can be, for example, expressed as a number of discrete time periods, such as weeks ("WEEKS") between the initial assessment and deadline date. The deadline date can be any date.

In step 630, a lowest allowable weight-two (LAW 2) is determined. LAW 2 may be calculated according to the general formula: LAW 2=BW−(BW*c*TIME) where c is a constant. In a more specific embodiment, where body weight loss is limited to 1.5% of body weight per week (i.e., c=0.015), the formula can be stated as: LAW 2=BW−(BW*0.015*TIME), where TIME is in units of weeks.

In step 640, a minimum weight (MW) is determined. The Minimum Weight may be calculated according to the following formula: MW=the higher of LAW 1 and LAW 2.

In step 650, minimum weight values for each of the discrete times in the measurement period may be calculated. The minimum weights can be calculated by reducing the alpha or initial body weight assessment by a percentage prescribed by a governing body. Reducing each preceding projected minimum weight by the percentage populates the projected weight fields in the forms described below.

FIG. 5 shows an exemplary embodiment of an weight assessment for a student athlete or other individual. The assessment form may comprise the following fields: last name; first name; gender; age; height; grade or level (if appropriate); hydration test pass/fail; date of assessment; alpha body weight (BW); and a plurality of assessment data. Assessment data may comprise some or all of the following: skinfold measurements; body fat percentage (BF %); body density (BD); fat weight (FW); fat free weight (FFW); target body fat percentage (TBF); and target weight (TW).

With regard to body fat measurements, if the skinfold method is used, the user completes a skinfold data entry section. The BF % will be calculated and read only. If hydrostatic, bod/pod, bioimpedance, or dexa methods are used to determine body fat, then the user will input the BF % as determined by that method directly into the form.

In one exemplary embodiment, skinfold measurements, if used, may be taken and entered from three locations on males (the triceps, abdominals, and subscapular area), and two locations on females (the triceps and subscapular area). The information collected is entered into the skinfold data entry section to the nearest millimeter with median values being calculated from each location. The median values are calculated based on the data inputted into each of the two or three skinfold sections. The sum median value skinfold (SumSF) is calculated by adding the three median values. The median values and SumSF are calculated, and should appear as read-only.

In one exemplary embodiment, body density (BD) is calculated as: $(1.0973-((SumSF)*0.000815))+(SumSF^2*0.00000084)$. BD is calculated, and should appear as read-only on the form.

Body Fat percentage (BF %) can be inputted directly by the user if a method other than skinfolds is used to determine BF %. Alternatively, it may be calculated for males as: $((4.57/BD)-4.142)*100$. For females, BF % may be calculated as: $[(Tricep\ SF+Subscapular\ SF)\times 1.33]-[(Tricep\ SF+Subscapular\ SF)^2\times 0.13]-2.5$.

Fat Weight (FW) is calculated as follows: BW*BF/100. This value should be read-only and is only calculated for males.

Fat Free Weight (FFW) is calculated as follows: BW−FW. This value should be read-only and is only calculated for males.

The Target Body Fat (TargetBF) the athlete wants to reach is entered into this step. In one embodiment, a minimum floor value may be imposed. For example, a value less than 7% for males and 12% for females may not be permitted to be entered.

Target Weight may then be calculated as follows:

For males: FFW/TargetBF (in one embodiment, the program will default to 7% if no data is entered into the target body fat field)

For females: (1−(% BF/100)*BW)/targetBF (in one embodiment, the program will default to 12% if no data is entered into the target body fat field).

The form also may contain an electronic signature area where the person who performed the assessment can enter their name along with the date. The form may further comprise a print and save option to save the form, and allow the user to print the form in a reportable report format. Separate save and print functions may also be available.

In one exemplary embodiment, upon a form being saved, a confirmation box may appear, and an option to add another athlete may be provided. Options to delete athletes or retrieve assessment data for a particular athlete also may be included.

In yet another exemplary embodiment, a variety of report options may be provided. Reports include the following:

Athletes or Students On File—This is a report that is created to show all school-age athletes that are on a given team, or students in a program or group. The following fields may appear on the report: name; year or level in school; alpha weight; target weight; a link to the athlete's weight management plan; a link to the athlete's assessment form; and a link to the athlete's ID number.

Weight Management Plan—This report is used to project permissible weight loss/gain for the school-age athlete. This form can be broken down daily or weekly depending on the state's request. In one exemplary embodiment, the permissible weight loss or gain per week is calculated using the formula: (BW*0.015). The BW is taken from the assessment form. This plan may be used as a weight gain form if the target weight is higher than the alpha weight.

The following fields may appear on the report: name; alpha weight; target weight; maximum weight loss/gain per week is calculated using the BW*0.015 formula; initial assessment date; date of the report; actual weight as of the time of the weigh-in (from the weigh-in reporting form); projected weight (based upon actual weight plus or minus the maximum weight loss/gain per week using the above formula); body fat percentage, and fat free weight. If the new actual weight recorded on a corresponding day is higher or lower than the projected weight, the weight management plan needs to re-calculate the new weight management plan using the actual weight substituted for BW (i.e., actual weight*0.015).

Alpha Master Report—The alpha master report is a compilation of all the assessments recorded onto one form for a particular school team. In essence, the alpha master report can be considered to be a team summary report. The alpha master report should contain all subsequent body fat, weight and fat free assessments under the name of each athlete so an easy comparison can be made at a quick glance. The alpha master report may contain the following information:
- A. School Name and Address—This information is created from the sport affiliation table after the master for the school is assigned.
- B. Name (Last, First)—Names are created after the initial assessment of the athlete.
- C. Alpha Date—Date that the athlete completed the initial assessment.
- D. Alpha Weight—Body weight on the date of the initial assessment.
- E. Alpha Body Fat—Body fat percentage that was calculated on the date of the initial assessment.
- F. Target Body Fat percentage—The target body fat percentage the athlete would like to reach. If no value was entered into the assessment form, this field should default to 7% for males and 12% for females, as described above.
- G. Target Weight—This is the target weight that the athlete would like to reach. This is calculated on the assessment form and reported on this report.
- H. First Date at Target Weight—This is the first date the athlete reaches his/her target weight. Using the formula (BW*0.015), the maximum weight loss/gain is determined. Subtracting or adding that value to the body weight until the target weight is reached may be used to determine the optimal number of days it takes to reach that value.

Student-Athlete Access Report—This report provides the login ID and passwords for each athlete on the school team to utilize the nutrition program. This will report may contain the following fields: school name and address (as above); first and last name of the athlete; alpha date (as above); alpha weight (as above); LoginID (the program may automatically generate a LoginID—in one exemplary embodiment, the LoginID is generated using the coach's masterID plus some other factor); and password. The password may be automatically generated using a formula. One exemplary formula is:

$$LCase(Mid([LastName],3,1)+Mid([FirstName],1,1)+Mid([LastName],1,1))+Right(Str(log(WrID+333)*10000000),4)$$

Weigh-In Data Entry Form—This report is used to input weight data for an athlete at a particular time (e.g., at a weigh-in). This form may contain the following information: date; name, calculated weight-management weight for that date (i.e., the weight the athlete should weigh on the date of the weigh-in; this weight is populated after the athlete's name is input or selected, such as from a drop-down list of athlete's for whom assessment data has been input); target body weight (the target weight the athlete wants to reach); and actual body weight (a blank field in which the actual weight of the athlete from the weigh-in should be entered). The form also may comprise an update button to cause the information in the form to be entered into the system.

After all weigh-in information is entered, the coach or other user may have the ability to print a report of all of the weigh-in information. A summary report may comprise the following data: date of weigh-in; athletes' names; weight-management weight; target weight; and actual weight.

Recalculation of Weight Management Form—The use of this form depends on whether the athlete is using the form as a weight loss plan or a weight gain plan. As a weight loss plan, if the athlete's actual weight is greater than the weight loss plan weight, the athlete's weight loss plan is recalculated using the new actual weight that was recorded on the weigh-in date. If the athlete's actual weight is less than or equal to the weight loss plan weight, the weight loss plan is not re-calculated. As a weight gain plan, if the athlete's actual weight is less than the weight gain plan weight, the athlete's weight gain plan is recalculated using the new actual weight that was recorded on the weigh-in date. If the athlete's actual weight is greater than or equal to the weight loss plan weight, the weight loss plan is not re-calculated.

In another exemplary embodiment, the general physical education/health assessment form comprises the following fields: first and last name; gender; a plurality of measurement fields (which may include height, weight, body mass index (BMI), subscapular skinfold measurement, triceps skinfold measurement, and waist circumference); weight body composition ranking (WBCR); health assessment grade; and target weight. Options to save and/or print the form may be provided.

In one exemplary embodiment, percentile rankings may be given for values in one or more measurement fields. Percentile rank may be given in relation to the population for boys and girls in the appropriate age range (e.g., 5 to 19). Reference data may be used from any appropriate source.

One appropriate source of reference data comprises the CDC's "Anthropometric Reference Data for Children and Adults: U.S. Population, 1999-2002". The original data in a source may be statistically "tuned" to provide a smooth progression across measurement values within an age and, where appropriate, across a range of ages. Accordingly, derived values may not correspond exactly to that found in the original source. Statistical manipulation attempts to smooth out outliers and oddities in the population originally selected for measurement. This technique may be used to smooth out rough edges by drawing a curve in the data space and rendering this curve in the form of equations that are easily processed by a computer. The present invention has derived equations that match the original CDC dataset with an error range (R squared) of 98% or better. The standard error of measurement is less than 5 in nearly all cases, and less than 6 in all cases. These simply reflect the fact that some datasets are a bit noisier than others with respect to the particular value being measured at particular age groups. These function are used by creating an object of type "RankAnalyze" and then calling the appropriate function with the argument for the current participant. Thus, in the one exemplary embodiment, the rank vs. population for a 12-year-old girl weight 100 pounds could be called using the following commands:

RankAnalyze ra=new RankAnalyze( );
int rank=ra. WeightRank(12, 100.0, RankAnalyze.gender.female);

In one exemplary embodiment of the physical education/health assessment form, BMI may be calculated as (Weight/Height$^2$). If weight is measured in kg, and height is measured in meters, BMI will be kg/m$^2$.

WBCR may be calculated using rank percentiles using the following formula: [(BMI percentile*5)+(S percentile*2)+(T percentile*2)+(WC percentile*1)]/10. The health assessment grade is then determined based on the calculated WBCR. In one embodiment, if the WBCR is below 75%, then the grade is "normal." If the WBCR is between 75% and 90%, then the grade is "at risk." If the WBCR is above 90%, then the grade is "overweight." Other labels may be used to characterize the health assessment grades.

The Target Weight (TW) calculation depends on the health assessment grade. If the grade is "at risk," then TW=Alpha Weight−(0.5 lbs*8 weeks). If the grade is "overweight," then TW=Alpha Weight−(1.0 lbs*8 weeks).

A variety of report options may be provided. Reports include the following:

Students on File—As shown in FIG. 7, this is a report that is created to show all students that that had assessments done for that class and/or masterID. The following fields may appear on the report: name; year or level in school; gender, alpha weight; target weight; a link to the student's summary assessment report; a link to the student's weight management plan; a link to the student's activity report; a link to the student's assessment form; and a link to the student's ID number.

Assessment Summary Report—The assessment summary report reports all previous assessments. Each time a new assessment is completed a new column or data area will be created. This will allow a teacher or assessor to view all the assessments to compare data. Data fields on the report may comprise the name and grade of the student, and for each assessment reported, the date of the assessment, weight, weight rank, height, height rank, BMI, BMI rank, waist circumference, waist circumference rank, triceps skinfold, triceps skinfold rank, subscapular skinfold, subscapular skinfold rank, WBCR, health assessment grade, and target weight.

Student Activity Report—In one exemplary embodiment, student athletes may record their activity level in a secured section on a website daily. The teacher or assessor will then be able to view the activity level for each student. The student activity report may comprise the following information: name of student; day of activity; activity category; activity classification; and duration of activity. A list providing a standard description of activities may be provided, as shown in FIG. 8.

Weight Management Plan—This report is to be used to project permissible weight loss/gain for the student. This form can be broken down daily or weekly. The body weight is taken from when the assessment was performed and is recorded during the completion of the assessment form. The value determined by the formula provides the permissible weight loss or gain for the student. The form serves as a weight gain form if the target weight is higher than the alpha weight. The information, including maximum weight loss/gain per week, may be calculated as described above.

Alpha Master Report—The alpha master report is compilation of all the assessments for a class or group recorded onto one form, and thus may be considered a class summary report. In one exemplary embodiment, the alpha master report comprises all subsequent body fat, weight, student's activity level and fat free assessments under or corresponding to the name of each student so an easy comparison can be made at a quick glance. The alpha master report may contain the same information, including health assessment grade, WBCR, and target weight, as described above.

Student Access Report—This report provides the login ID and passwords for each student to utilize the nutrition program. This will report main contain the following fields: school name and address; last and first name of the student; alpha date (date of initial assessment); alpha weight (date of the initial assessment); LoginID (as above); and password (as above).

Weigh-In Data Entry Forms and Recalculation of Weight Management Forms also may be used, each form corresponding to the form of the same name as described above.

Thus, it should be understood that the embodiments and examples have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art, and variations and changes may be made by those skilled in the art without departing from the spirit of the invention.

We claim:

1. A system for conducting a weight assessment and classification program over a network, comprising:
    one or more servers connected to the network;
    one or more databases on said server or servers;
    a data entry program, said program providing a menu of data entry options on a user access port connected to the network, at least one of the data entry options allowing entry of data for generating an assessment of a subject, said data being stored in one or more of said databases;
    further wherein said system determines a weight-based classification rating for the subject based on the percentile ranking of the subject in relation to reference group:
    further wherein said system generates a weight plan on a server connected to the network based on the subject assessment data and weight-based classification rating, the weight plan including a plurality of target weights for the subject, each of the target weights being associated with a time, and further wherein the weight plan is generated by a method comprising:
        (a) determining a first minimum target weight using the subject's body weight, body fat percentage, and fat weight; and
        (b) iteratively decreasing the first minimum target weight by a constant factor, each successive decrease in the first minimum target weight corresponding to a successive minimum target weight for a successive time period; and further wherein said system further comprises an option to appeal a weight plan to a governing body.

2. The system of claim 1, the method of generating the weight plan further comprising the step of: allowing entry of data concerning activity of the subject.

3. The system of claim 1, the method of generating the weight plan further comprising the steps of:
    generating a nutritional plan based on the subject data entered, wherein generating the nutrition plan comprises:
    providing a series of food exchange item displays to the user;
    receiving food exchange item selections from the user; and generating a nutritional plan based on the selections.

4. The system of claim 1, wherein the body fat percentage is calculated as [4.57/body density−4.142]*100.

5. The system of claim 1, wherein fat weight is calculated as: [subject's body weight*(body fat percentage/100)].

6. The system of claim 1, wherein the first minimum weight value is calculated as the larger of: [(fat free weight/f) and ((subject's body weight)−(subject's body weight*c*time))])], where f is a factor that describes the minimum body fat allowed and c is a constant that describes the maximum body weight loss per time period as a factor of body weight.

7. The system of claim 1, wherein subject data entry options include skinfold measurements.

8. The system of claim 1, further comprising a user interface for monitoring the subject's weight over the network.

9. The system of claim 1, wherein generating the weight plan comprises the steps of:

determining a first minimum target weight using the subject's body mass index, triceps skinfold measurements, and subscapular skinfold measurements; and iteratively decreasing the first minimum target weight by a constant factor, each successive decrease in the first minimum target weight corresponding to a successive minimum target weight for a successive time period.

10. The system of claim 8, wherein the subject's weight is monitored by someone other than the subject.

11. The system of claim 8, wherein the step of monitoring comprises receiving actual weight data about the subject, and comparing the actual weight data to a corresponding target weight generated by the weight plan.

12. The system of claim 11, further wherein the step of monitoring comprises modifying the weight plan based upon the comparison of the actual weight data to a corresponding target weight.

13. The system of claim 12, wherein the modification of the weight plan comprises recalculating a new series of targets weights going forward using the actual weight substituted for the initial body weight or the weight last used to calculate or modify the weight plan.

14. The system of claim 12, wherein the weight plan is modified only if the actual weight is greater than the corresponding target weight where the weight plan is a weight loss plan, or if the actual weight is less than the corresponding target weight where the weight plan is a weight gain plan.

15. The system of claim 11, wherein the actual weight data is weight data measured at a weigh-in for a subject that is an athlete.

16. The system of claim 1 wherein the constant factor is 0.015.

17. The system of claim 1 wherein the weight-based classification is determined from the subject's height, weight, body mass index, triceps skinfold measurements, subscapular skinfold measurements, waist circumference, and percentage of body fat.

18. The system of claim 1 wherein the system is capable of generating an alpha master report for a school comprising:
  A. an alpha weight and/or an alpha body fat for each student assessed by the school;
  B. a target weight and/or a target body fat for each student assessed by the school; and
  C. a first date at which the target weight or target body fat may be met by each student assessed by the school.

19. The system of claim 18 wherein the system is further capable of generating report comprising a weight management plan for each student assessed by the school.

* * * * *